(12) United States Patent
Ueda et al.

(10) Patent No.: US 12,213,692 B2
(45) Date of Patent: Feb. 4, 2025

(54) TREATMENT TOOL FOR ENDOSCOPE

(71) Applicant: FUJIFILM Corporation, Tokyo (JP)

(72) Inventors: Yoshihiro Ueda, Kanagawa (JP);
Keiichiro Takahashi, Kanagawa (JP);
Jun Sato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 430 days.

(21) Appl. No.: 17/665,729

(22) Filed: Feb. 7, 2022

(65) Prior Publication Data

US 2022/0151651 A1    May 19, 2022

Related U.S. Application Data

(63) Continuation of application No. PCT/JP2020/033686, filed on Sep. 4, 2020.
(Continued)

(51) Int. Cl.
*A61B 17/29* (2006.01)

(52) U.S. Cl.
CPC .. *A61B 17/2909* (2013.01); *A61B 2017/2905* (2013.01); *A61B 2017/2916* (2013.01); *A61B 2017/2946* (2013.01)

(58) Field of Classification Search
CPC ........ A61B 17/2909; A61B 2017/2905; A61B 2017/2916; A61B 2017/2946; A61B 2017/00269; A61B 2017/00309; A61B 2017/00314; A61B 2017/0034; A61B 2017/2929; A61B 2017/2937; A61B 17/29; A61B 18/1445; A61B 18/1447;
(Continued)

(56) References Cited

U.S. PATENT DOCUMENTS 5,490,819 A * 2/1996 Nicholas .................. A61B 1/32
606/205
6,458,074 B1 10/2002 Matsui et al.
(Continued)

FOREIGN PATENT DOCUMENTS

JP   H09-262239 A   10/1997
JP   2001-212078 A   8/2001
(Continued)

OTHER PUBLICATIONS

International Search Report issued in PCT/JP2020/033686; mailed Dec. 1, 2020.
(Continued)

*Primary Examiner* — Mohamed G Gabr
*Assistant Examiner* — Aman Kumar Mann
(74) *Attorney, Agent, or Firm* — Studebaker & Brackett PC

(57) ABSTRACT

A treatment tool for an endoscope includes an operating part and a transmitting part that transmits an operation of the operating part to a grip part of a distal end part and a bendable part. The operating part has an operating member that is movable in a first direction and a second direction orthogonal to the first direction. The transmitting part has a first transmitting member that is moved to an operating part side based on an operation of the operating member in the first direction and closes the grip part and a second transmitting member that is moved to the operating part side based on an operation of the operating member in the second direction and bends the bendable part.

8 Claims, 42 Drawing Sheets

Related U.S. Application Data

(60) Provisional application No. 63/064,899, filed on Aug. 12, 2020, provisional application No. 62/896,579, filed on Sep. 6, 2019.

(58) Field of Classification Search
CPC ........ A61B 18/1442; A61B 2017/2927; A61B 2017/291; A61B 2017/2932; A61B 2017/2933; A61B 2017/2936; A61B 2017/00296; A61B 2017/00292; A61B 2017/003; A61B 2017/00327; A61B 2017/00318; A61B 2017/2913; A61B 2017/2912; A61B 10/06; A61B 17/3201; A61B 2018/146; A61B 2018/1457; A61B 2018/1455; A61B 2018/1452
See application file for complete search history.

(56) References Cited

U.S. PATENT DOCUMENTS

| | | |
|---|---|---|
| 2009/0054733 A1 | 2/2009 | Marescaux et al. |
| 2009/0054734 A1 | 2/2009 | DeSantis et al. |
| 2009/0312773 A1* | 12/2009 | Cabrera ............. A61B 17/0469 606/144 |
| 2012/0245414 A1 | 9/2012 | Verbeek |
| 2013/0012929 A1 | 1/2013 | Malkowski |
| 2015/0066022 A1* | 3/2015 | Shelton, IV ......... A61B 18/082 606/41 |
| 2015/0282788 A1 | 10/2015 | Chen et al. |
| 2017/0119417 A1* | 5/2017 | Kappus ............ A61B 17/00234 |
| 2020/0345446 A1* | 11/2020 | Kimball ................. A61B 90/08 |

FOREIGN PATENT DOCUMENTS

| | | |
|---|---|---|
| JP | 2002-330973 A | 11/2002 |
| JP | 2009-50697 A | 3/2009 |
| JP | 2009-101134 A | 5/2009 |
| JP | 2012-105793 A | 6/2012 |

OTHER PUBLICATIONS

Written Opinion issued in PCT/JP2020/033686; mailed Dec. 1, 2020.

An Office Action; "Notice of Reasons for Refusal," mailed by the Japanese Patent Office on Jan. 24, 2023, which corresponds to Japanese Patent Application No. 2021-544069 and is related to U.S. Appl. No. 17/665,729; with English language translation.

* cited by examiner

FIG. 16
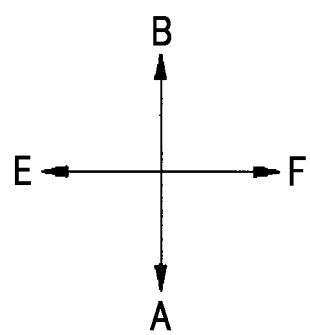
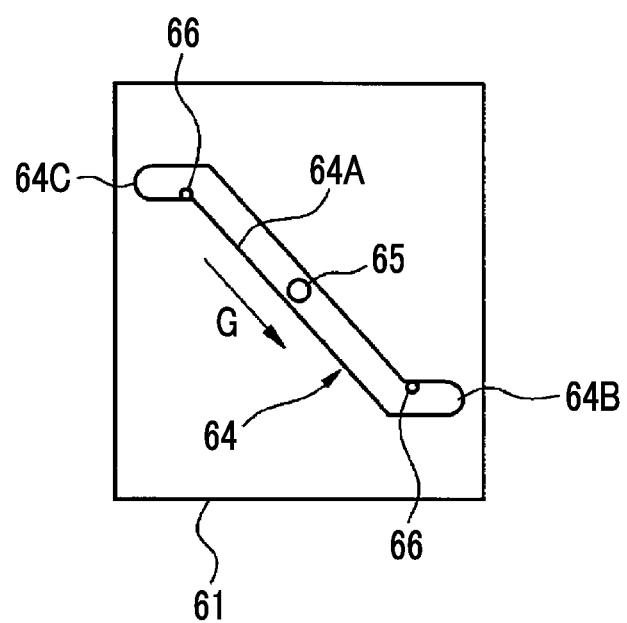

FIG. 19
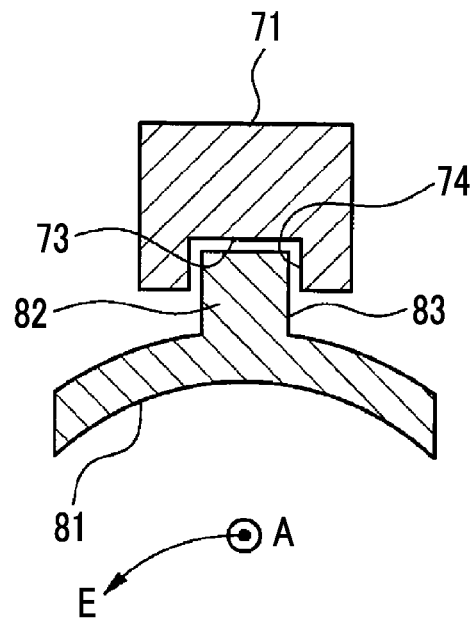
FIG. 20
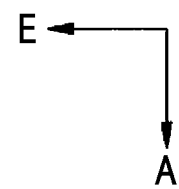
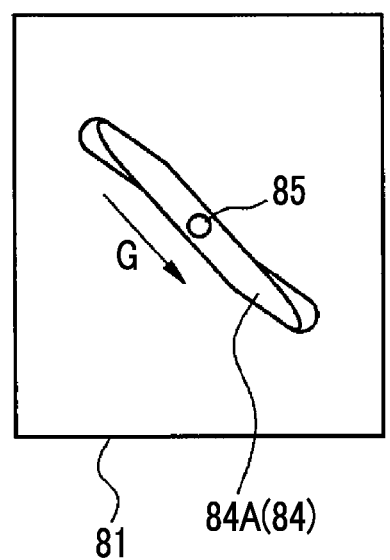

TREATMENT TOOL FOR ENDOSCOPE

CROSS REFERENCE TO RELATED APPLICATION

This is a continuation of International Application No. PCT/JP2020/033686 filed on Sep. 4, 2020, and claims priority from U.S. Provisional Application No. 62/896,579 filed on Sep. 6, 2019 and U.S. Provisional Application No. 63/064,899 filed on Aug. 12, 2020, the entire disclosures of which are incorporated herein by reference.

BACKGROUND OF THE INVENTION

1. Field of the Invention

The present invention relates to a treatment tool for an endoscope.

2. Description of the Related Art

Various types of treatment are performed on a living body by combining an endoscope and a treatment tool for an endoscope. As an example of treatment, endoscopic submucosal dissection (ESD) is known. An interior wall such as the esophagus, stomach, and large intestine to which ESD is applied consists of three layers including a mucous membrane layer, a submucosal layer, and a muscular layer. In ESD, a lesion part of the mucous membrane layer including the submucosal layer is peeled off, and it is also possible to collectively excise, for example, a relatively large lesion part which exceeds 2 cm.

An endoscope described in JP2001-212078A is used in, for example, ESD, and comprises a first treatment tool insertion channel and a second treatment tool insertion channel. The first treatment tool insertion channel is open to a distal end of an insertion part of the endoscope, and a first erecting mechanism that erects a treatment tool in a first direction (for example, an up-and-down direction) is provided at a distal end opening portion of the first treatment tool insertion channel. Also the second treatment tool insertion channel is open to the distal end of the insertion part of the endoscope, and a second erecting mechanism that erects the treatment tool in a second direction (for example, a right-and-left direction) different from the first direction is provided at a distal end opening portion of the second treatment tool channel.

In a case where the endoscope described in JP2001-212078A is used in ESD, a grip forcep is inserted into the first treatment tool insertion channel, and an incision tool such as an electric scalpel is inserted into the second treatment tool insertion channel. The grip forcep and the incision tool approach a lesion part from the side of the lesion part along the interior wall. First, as the lesion part is gripped by the grip forcep and the grip forcep gripping the lesion part is erected by the first erecting mechanism of the endoscope, the lesion part is lifted. Then, as a lower part of the lifted lesion part is incised by the incision tool and the incision tool is swung right and left by the second erecting mechanism of the endoscope, incision proceeds. In this manner, the lesion part including the submucosal layer is gradually peeled off.

In addition, also a treatment tool for an endoscope that can perform treatment including both of gripping and incision is known. A treatment tool for an endoscope described in JP2002-330973A comprises a sheath, a forcep member provided at a distal end part of the sheath, and a high-frequency knife inserted in the sheath. The forcep member is opened and closed by a first operating part provided at a proximal end part of the sheath. The high-frequency knife protrudes from between a pair of arm portions of the forcep member and is moved forward and backward in an axial direction of the sheath by a second operating part provided at the proximal end part of the sheath.

SUMMARY OF THE INVENTION

In the endoscope described in JP2001-212078A, in order to grip and lift the lesion part, an operation of the grip forcep for gripping the lesion part and an operation of the endoscope for erecting the grip forcep are necessary, thereby complicating the operation.

The treatment tool for an endoscope described in JP2002-330973A can only pull the lesion part gripped by the forcep member in the axial direction of the sheath with an operation of the treatment tool alone. A bending operation of the endoscope is necessary to lift the lesion part, and the visual field of the endoscope moves in response to the bending operation of the endoscope, thereby increasing the difficulty of treatment.

The present invention is devised in view of the circumstances described above, and an object thereof is to provide a treatment tool for an endoscope that can easily perform gripping of a lesion part and lifting of the gripped lesion part with an operation of the treatment tool alone.

According to an aspect of the present invention, there is provided a treatment tool for an endoscope comprising an insertion part that has a distal end part which is provided with an openable and closable grip part and a bendable part, which is provided adjacent to the distal end part and is bendable, and that is insertable into a body, an operating part into which an operation of closing the grip part and an operation of bending the bendable part are input, and a transmitting part that transmits the operations of the operating part to the grip part and the bendable part. The operating part has an operating member that is movable in a first direction parallel to a longitudinal axis of the insertion part and a second direction orthogonal to the first direction. The transmitting part has a follower member that is movable only in the first direction among the first direction and the second direction, a cam member that is movable only in the second direction among the first direction and the second direction and drives the follower member in the first direction in response to a movement in the second direction, a first transmitting member that extends from the operating member to the insertion part, and a second transmitting member that extends from the follower member to the insertion part. The operating member and the cam member have engaging parts respectively that allow a relative movement in the first direction and prevent a relative movement in the second direction by engaging with each other. The grip part is closed as any one of the first transmitting member or the second transmitting member is moved in the first direction. The bendable part is bent as the other one of the first transmitting member or the second transmitting member is moved in the first direction. According to another aspect of the present invention, there is provided a treatment tool for an endoscope comprising an insertion part that has a distal end part which is provided with an openable and closable grip part and a bendable part, which is provided adjacent to the distal end part and is bendable, and that is insertable into a body, an operating part into which an operation of closing the grip part and an operation of bending the bendable part are input, and a transmitting part that transmits the operations of the operating part to the grip part and the bendable part. The operating part has a gripped part that is gripped by a user and a lever part that is capable of being tilted with respect to the gripped part with an operation by a thumb of a hand of the user gripping the gripped part. The transmitting part has a first transmitting member that moves in the first direction according to tilting of the lever part in a second direction orthogonal to a first direction parallel to a longitudinal axis of the insertion part and a second transmitting member that moves in the first direction according to tilting of the lever part in a third direction orthogonal to the first direction and the second direction. The grip part is closed as the first transmitting member is moved in the first direction. The bendable part is bent as the second transmitting member is moved in the first direction.

With the present invention, it is possible to provide the treatment tool for an endoscope that can easily perform gripping of a lesion part and lifting of the gripped lesion part with an operation of the treatment tool alone.

BRIEF DESCRIPTION OF THE DRAWINGS

FIG. 16 is a view showing a modification example of the cam groove of FIG. 12.

FIG. 19 is a view showing an engaging part of the transmitting part of FIG. 18.

FIG. 20 is a view showing a cam groove of the transmitting part of FIG. 18.

DESCRIPTION OF THE PREFERRED EMBODIMENTS

Embodiment 1

Figure 1:
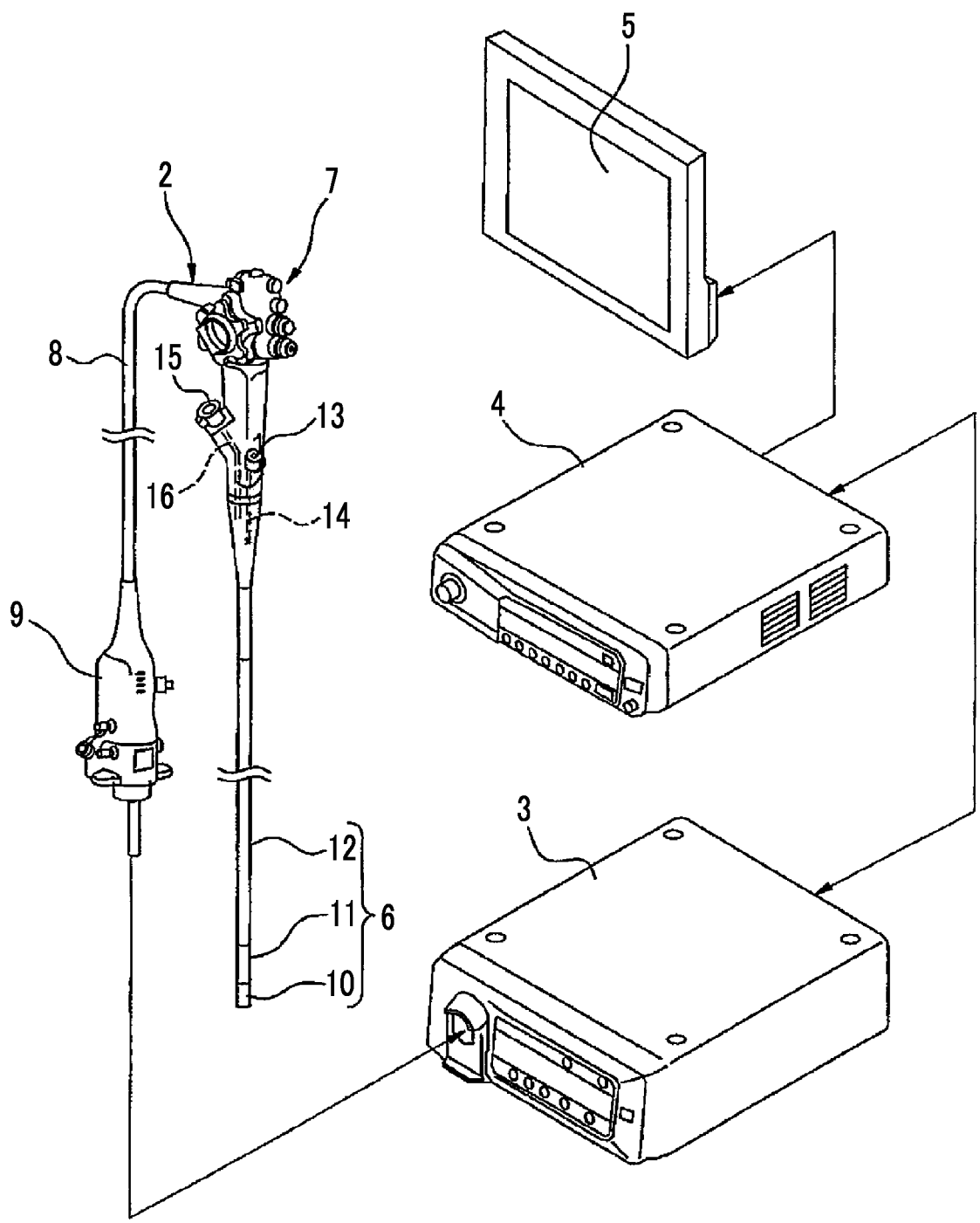
FIG. 1 is a view showing an example of an endoscope system, which is for describing Embodiment 1 of the present invention.

FIG. 1 shows an example of an endoscope system for describing Embodiment 1 of the present invention.

An endoscope system 1 comprises an endoscope 2, a light source device 3, and a processor 4. The endoscope 2 has an endoscope insertion part 6 that is inserted into a subject, an endoscope operating part 7 that is connected to the endoscope insertion part 6, and a universal cord 8 that extends from the endoscope operating part 7. The endoscope insertion part 6 is composed of an endoscope distal end part 10, an endoscope bendable part 11 that is connected to the endoscope distal end part 10, and an endoscope soft portion 12 that connects the endoscope bendable part 11 to the endoscope operating part 7.

An imaging apparatus including an imaging element is mounted on the endoscope distal end part 10. The endoscope bendable part 11 is configured to be bendable, and the bending of the endoscope bendable part 11 is operated by the endoscope operating part 7. In addition, the endoscope soft portion 12 is soft enough to be deformable along a shape of an insertion passage in the subject.

The endoscope operating part 7 is provided with an operation button for operating image pick-up using the imaging apparatus and an operation knob for operating the bending of the endoscope bendable part 11. In addition, the endoscope operating part 7 is provided with a first treatment tool insertion opening 13 and a second treatment tool insertion opening 15, into which the treatment tool for an endoscope is insertable. Inside the endoscope insertion part 6, a first treatment tool channel 14 that reaches the endoscope distal end part 10 from the first treatment tool insertion opening 13 and is open to an edge surface of the endoscope distal end part 10 and a second treatment tool channel 16 that reaches the endoscope distal end part 10 from the second treatment tool insertion opening 15 and is open to the edge surface of the endoscope distal end part 10 are provided.

A light guide and a cable are provided inside the endoscope insertion part 6, the endoscope operating part 7, and the universal cord 8. A connector 9 is provided at a terminal of the universal cord 8. The endoscope 2 is connected to the light source device 3 and the processor 4 via the connector 9.

Illumination light generated by the light source device 3 is guided to the endoscope distal end part 10 via the light guide and is emitted from the endoscope distal end part 10. In addition, operating power of the imaging element, a control signal for driving the imaging element, and an image signal output from the imaging element are transmitted between the processor 4 and the imaging apparatus via the cable. The processor 4 processes the input image signal to generate image data of an observation site in the subject, displays the generated image data on a monitor 5, and records the generated image data.

Figure 2:
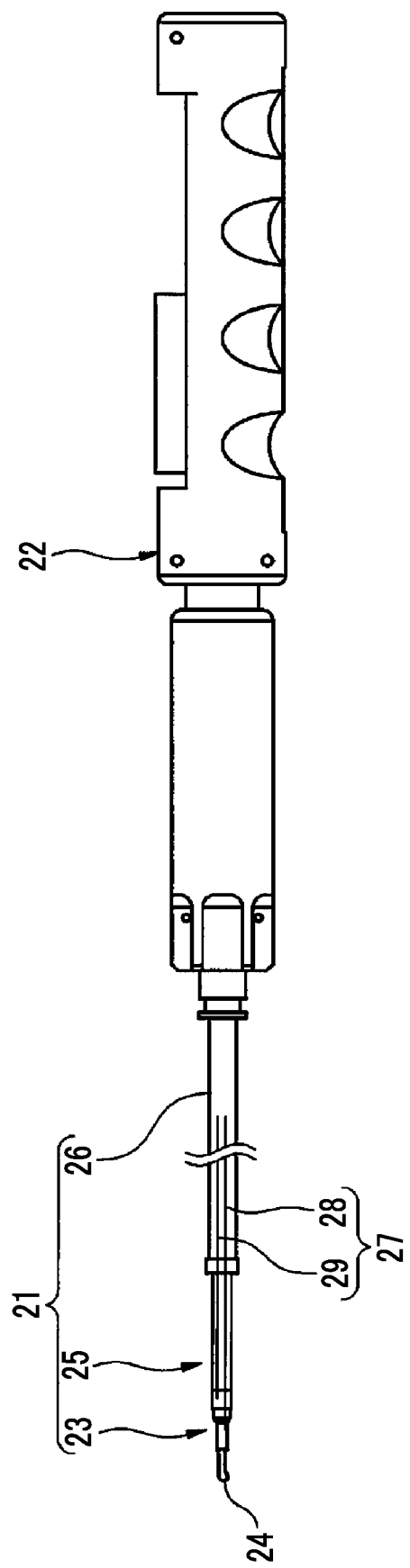
FIG. 2 is a view showing an example of a treatment tool for an endoscope, which is for describing Embodiment 1 of the present invention.

FIG. 2 shows an example of the treatment tool for an endoscope, which is for describing Embodiment 1 of the present invention.

A treatment tool for an endoscope 20 comprises an insertion part 21 that can be inserted into the first treatment tool channel 14 (see FIG. 1) and an operating part 22. The insertion part 21 has a distal end part 23 at which an openable and closable grip part 24 is provided, a bendable part 25 that is provided adjacent to an operating part side of the distal end part 23 and is bendable, and a soft portion 26 that connects the bendable part 25 to the operating part 22.

In a case where the insertion part 21 is inserted in the first treatment tool channel 14, the distal end part 23 and the bendable part 25 protrude from the edge surface of the endoscope distal end part 10 (see FIG. 1), and the soft portion 26 is accommodated in the first treatment tool channel 14. Similar to the endoscope soft portion 12, the soft portion 26 accommodated in the first treatment tool channel 14 is soft enough to be deformable along the shape of the insertion passage in the subject. The soft portion 26 can be configured, for example, such that an outer periphery of a screw pipe, which is formed by spirally winding a metal strip plate material, is covered with a mesh pipe formed by braiding a metal wire and an outer periphery of the mesh pipe is covered with a resin outer coat.

An operation of closing the grip part 24 (hereinafter, referred to as a closing operation) and an operation of bending the bendable part 25 (hereinafter, referred to as a bending operation) are input into the operating part 22. The treatment tool for an endoscope 20 further comprises a transmitting part 27 that transmits the operations of the operating part 22 to the grip part 24 and the bendable part 25. The transmitting part 27 has a first transmitting member 28 that extends from the grip part 24 toward the operating part 22 and a second transmitting member 29 that extends from the bendable part 25 toward the operating part 22. The first transmitting member 28 and the second transmitting member 29 are accommodated inside the soft portion 26. The closing operation input into the operating part 22 is transmitted to the grip part 24 via the first transmitting member 28, and the bending operation input into the operating part 22 is transmitted to the bendable part 25 via the second transmitting member 29.

Figure 3:
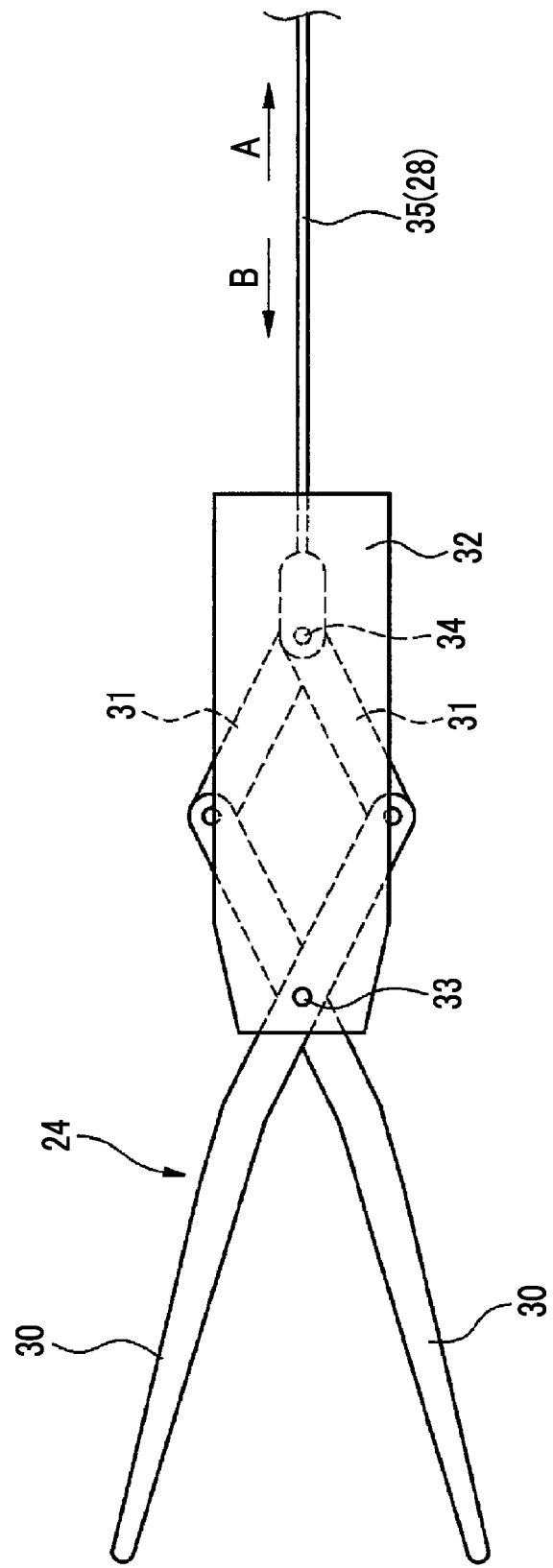
FIG. 3 is a view showing a grip part of the treatment tool for an endoscope of FIG. 2.
Figure 4:
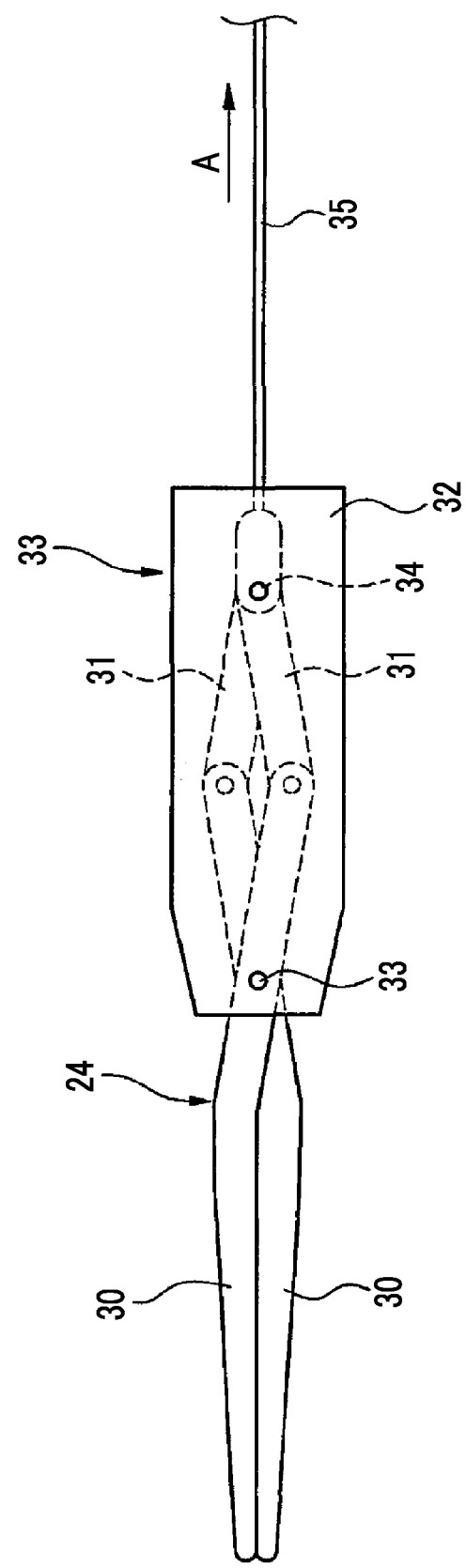
FIG. 4 is a view showing an operation of the grip part of FIG. 3.

FIGS. 3 and 4 show the grip part 24.

The grip part 24 has a pair of grip claws 30, a pair of link members 31, and a support 32 that supports the pair of grip claws 30 so as to be movable rotationally. The pair of grip claws 30 are disposed to intersect each other, and a pin 33 is provided to penetrate an intersecting portion of the pair of grip claws 30. The pair of grip claws 30 are movable rotationally about the pin 33 which is a rotational movement shaft, and the pin 33 is fixed to the support 32.

A distal end part of each of the pair of link members 31 is connected to a proximal end part of each of the pair of grip claws 30 so as to be movable rotationally. A proximal end part of each of the pair of link members 31 is disposed to intersect each other, and a pin 34 is provided to penetrate an intersecting portion of the pair of link members 31. The pair of link members 31 are movable rotationally about the pin 34 which is a rotational movement shaft, and the pin 34 is movable to increase or decrease a distance to the pin 33 instead of being fixed to the support 32.

As the first transmitting member 28 that transmits an operation of the operating part 22 to the grip part 24, one wire 35 is used in the present example, and a distal end part of the wire 35 is connected to the pin 34. The wire 35 is pulled to an operating part 22 side based on the operation of the operating part 22. Herein, as for movement of the wire 35, pulling to the operating part 22 side is defined as a movement in an A-direction, and pushing out to a distal end part 23 side is defined as a movement in a B-direction.

FIG. 3 shows a state where the wire 35 is pushed out to the distal end part 23 side, and the distal end parts of the pair of grip claws 30 are open. By moving the wire 35 in the A-direction (first direction) based on an operation of the operating part 22, the distal end parts of the pair of grip claws 30 are closed as shown in FIG. 4. On the other hand, by moving the wire 35 in the B-direction (second direction) in a state where the distal end parts of the pair of grip claws 30 are closed, the distal end parts of the pair of grip claws 30 are opened.

The wire 35 is an example of the first transmitting member 28, and the first transmitting member 28 may be an object that has flexibility, which does not hinder the bending of the bendable part 25 and the deformation of the soft portion 26, and can transmit a force in the A-direction and the B-direction, and may be, for example, a coil spring. In addition, the first transmitting member 28 may be a tube that is filled with a working fluid therein and is provided with a piston at the distal end part thereof.

Figure 5:
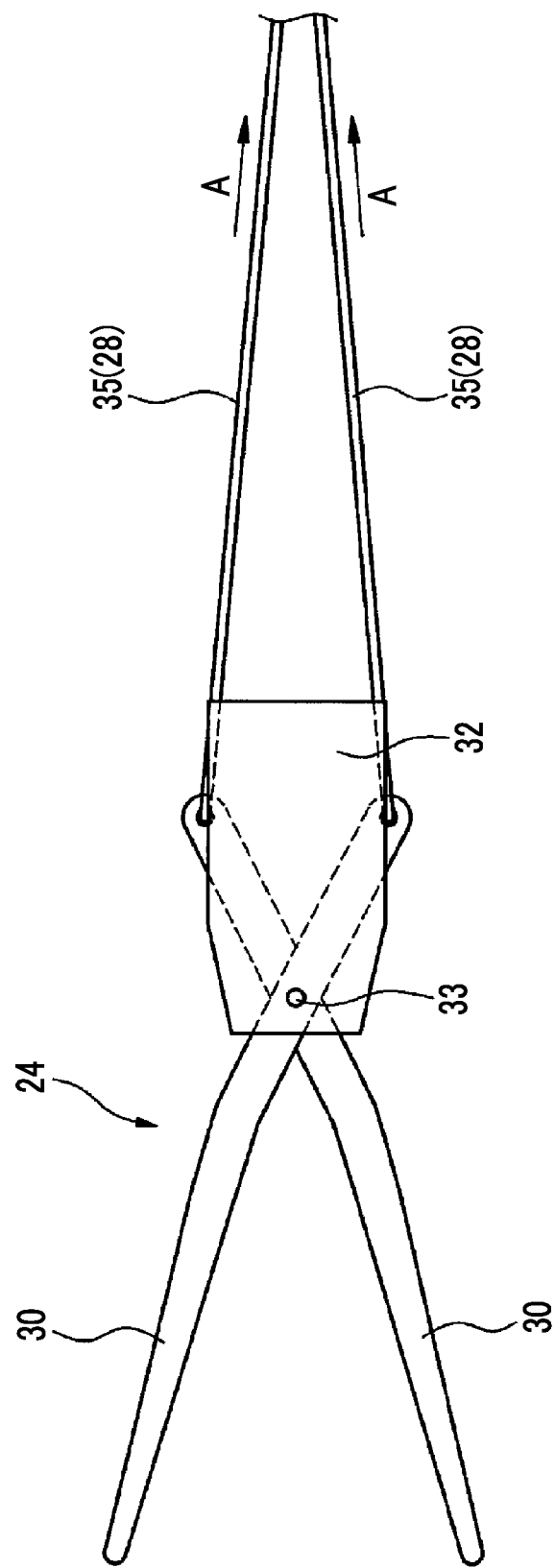
FIG. 5 is a view showing a modification example of the grip part of FIG. 3.

FIG. 5 shows another example of the grip part 24. Two wires 35 are used as the first transmitting member 28, and the wires 35 are connected to the proximal end parts of the pair of grip claws 30, respectively. By moving two wires 35 in the A-direction, the distal end parts of the pair of grip claws 30 are closed. In the example shown in FIG. 5, the pair of link members 31 are unnecessary, and the length of the distal end part 23 can be reduced. Instead of the two wires 35, a single wire of which a distal end side is branched into two may be used, which is advantageous in reducing the diameters of the bendable part 25 and the soft portion 26.

Figure 6:
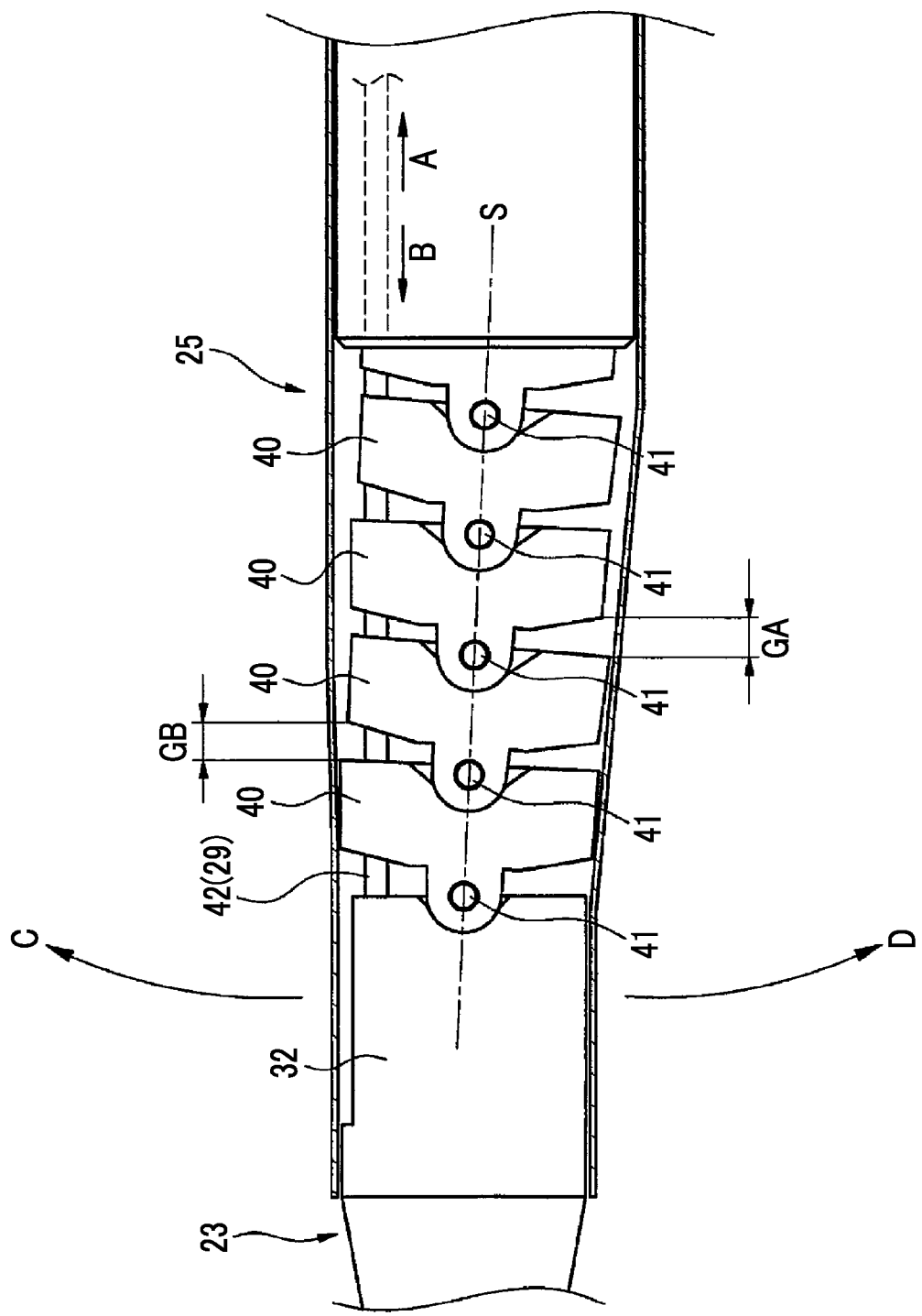
FIG. 6 is a view showing a bendable part of the treatment tool for an endoscope of FIG. 2.
Figure 7:
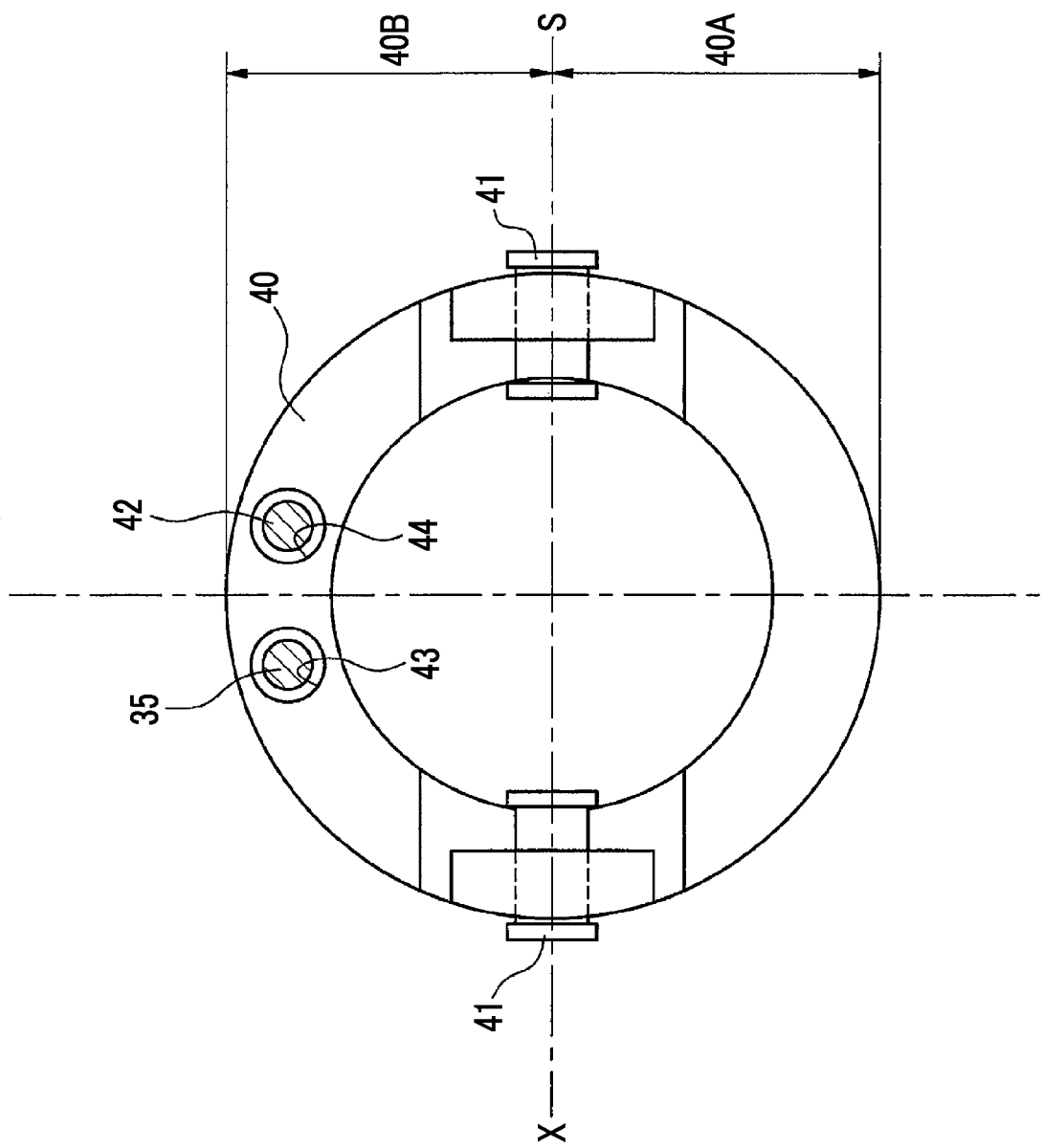
FIG. 7 is a view showing a cross section of the bendable part of FIG. 6.
Figure 8:
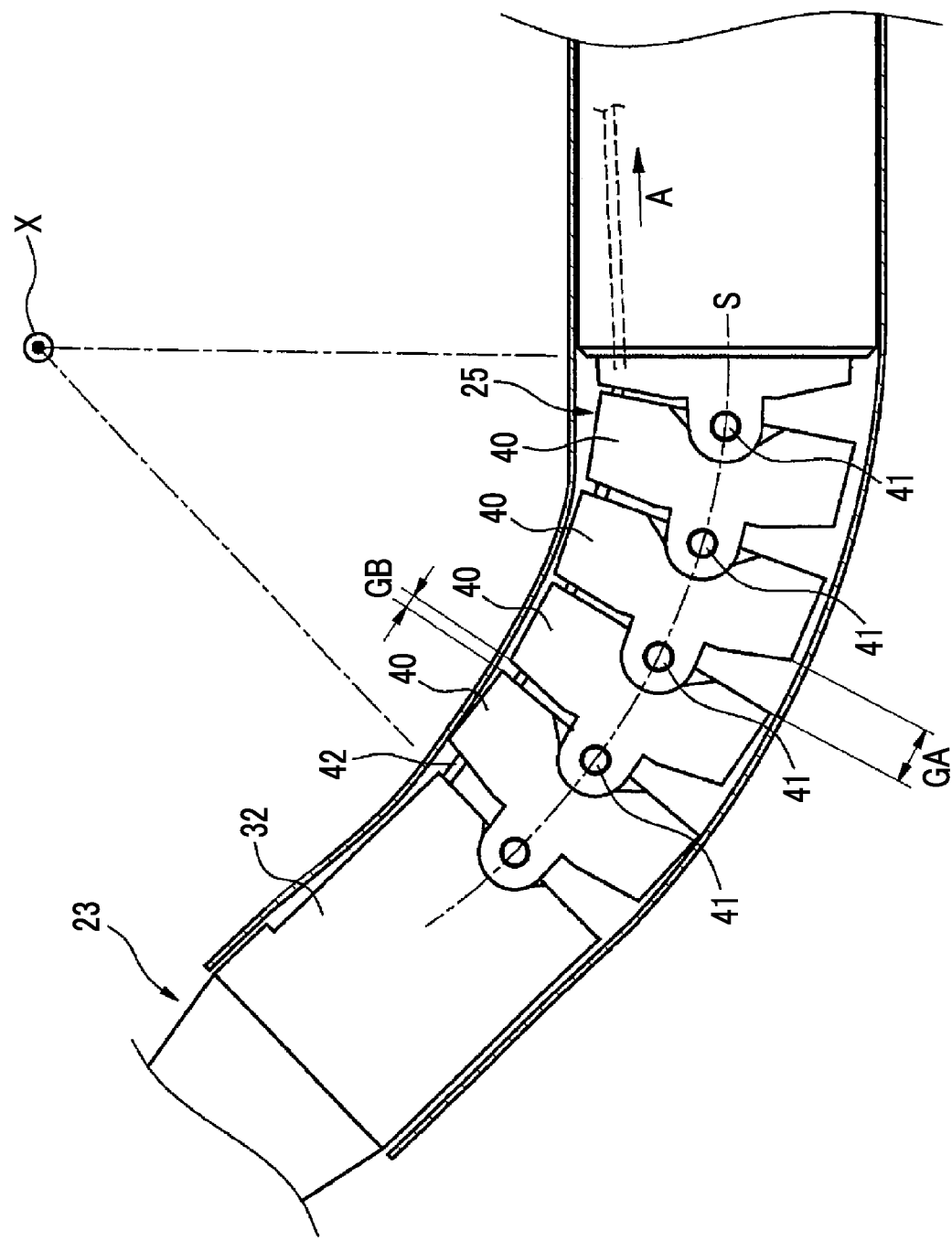
FIG. 8 is a view showing an operation of the bendable part of FIG. 6.

FIGS. 6 to 8 show the bendable part 25.

The bendable part 25 has a plurality of cyclic members 40 arranged in an axial direction of the insertion part 21, and two cyclic members 40, which are adjacent to each other, are connected to each other by a pair of pins 41. The two cyclic members 40 connected to each other by the pair of pins 41 are movable rotationally with respect to each other about a rotational movement shaft x passing through the pair of pins 41. The bending of the bendable part 25 is the sum of the rotational movements of the plurality of cyclic members 40. A bending central axis X for the bending of the bendable part 25 is parallel to the rotational movement shaft x, and is parallel to an opening and closing direction of the pair of grip claws 30.

A plane of which a length along a central axis of the insertion part 21 is constant regardless of the bending of the bendable part 25 is defined as a bent neutral plane, and a bent neutral plane S of the bendable part 25 passes through the plurality of pins 41 arranged in the axial direction of the insertion part 21. In a case where the cyclic member 40 is divided into a first portion 40A and a second portion 40B with the bent neutral plane S as a boundary, there is a gap GA between the first portions 40A of the two cyclic members 40 adjacent to each other, and there is a gap GB also between the second portions 40B. Therefore, the bendable part 25 is bendable in a C-direction in which the gap GB on a second portion 40B side is narrowed, and is bendable also in a D-direction in which the gap GA on a first portion 40A side is narrowed.

The bendable part 25 is bendable in both directions including the C-direction and the D-direction, but is bent in the C-direction based on an operation of the operating part 22. As the second transmitting member 29 that transmits the operation of the operating part 22 to the bendable part 25, a wire 42 is used in the present example, and a distal end part of the wire 42 is fixed to the support 32 of the distal end part 23. The wire 42 is pulled to the operating part 22 side based on the operation of the operating part 22. Herein, as for a movement of the wire 42, pulling to the operating part 22 side is defined as a movement in the A-direction, and pushing out to the distal end part 23 side is defined as a movement in the B-direction.

In the bending of the bendable part 25 in the C-direction, the first portion 40A of the cyclic member 40 is positioned on a bent outer diameter side, and the second portion 40B is positioned on a bent inner diameter side. In the second portion 40B positioned on the bent inner diameter side, a first guide 43 and a second guide 44 are provided. The first guide 43 and the second guide 44 each are a hole that penetrates the second portion 40B in the axial direction of the insertion part 21, the wire 35 is inserted in the first guide 43, and the wire 42 is inserted in the second guide 44. The wire 35 inserted in the first guide 43 and the wire 42 inserted in the second guide 44 are disposed on the bent inner diameter side in the bending of the bendable part 25 in the C-direction. The first guide 43 and the second guide 44 are not limited to the holes insofar as the wire 35 and the wire 42 can be held so as to be able to be pushed and pulled in the axial direction of the insertion part 21.

As the wire 42 is moved in the A-direction (first direction) based on an operation of the operating part 22, the gap GB on the second portion 40B side, which is between the two cyclic members 40 adjacent to each other, is narrowed, and the bendable part 25 is bent in the C-direction. On the other hand, as the wire 42 is moved in the B-direction in a state where the bendable part 25 is bent in the C-direction, the bendable part 25 is extended in a linear shape.

The wire 42 is an example of the second transmitting member 29, and the second transmitting member 29 may be an object that has flexibility, which does not hinder the bending of the bendable part 25 and the deformation of the soft portion 26, and can transmit a force in the A-direction and the B-direction, and may be, for example, a coil spring. In addition, the second transmitting member 29 may be a tube that is filled with a working fluid therein and is provided with a piston at the distal end part thereof.

Figure 9:
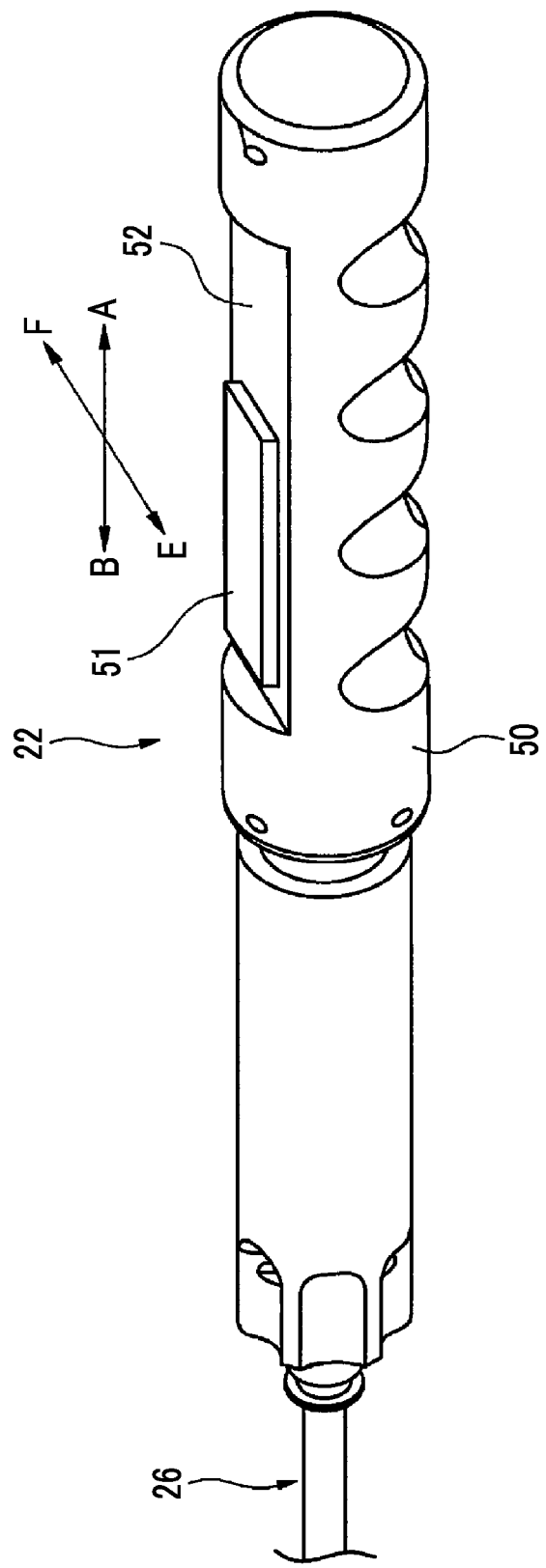
FIG. 9 is a view showing an operating part of the treatment tool for an endoscope of FIG. 2.
Figure 10:
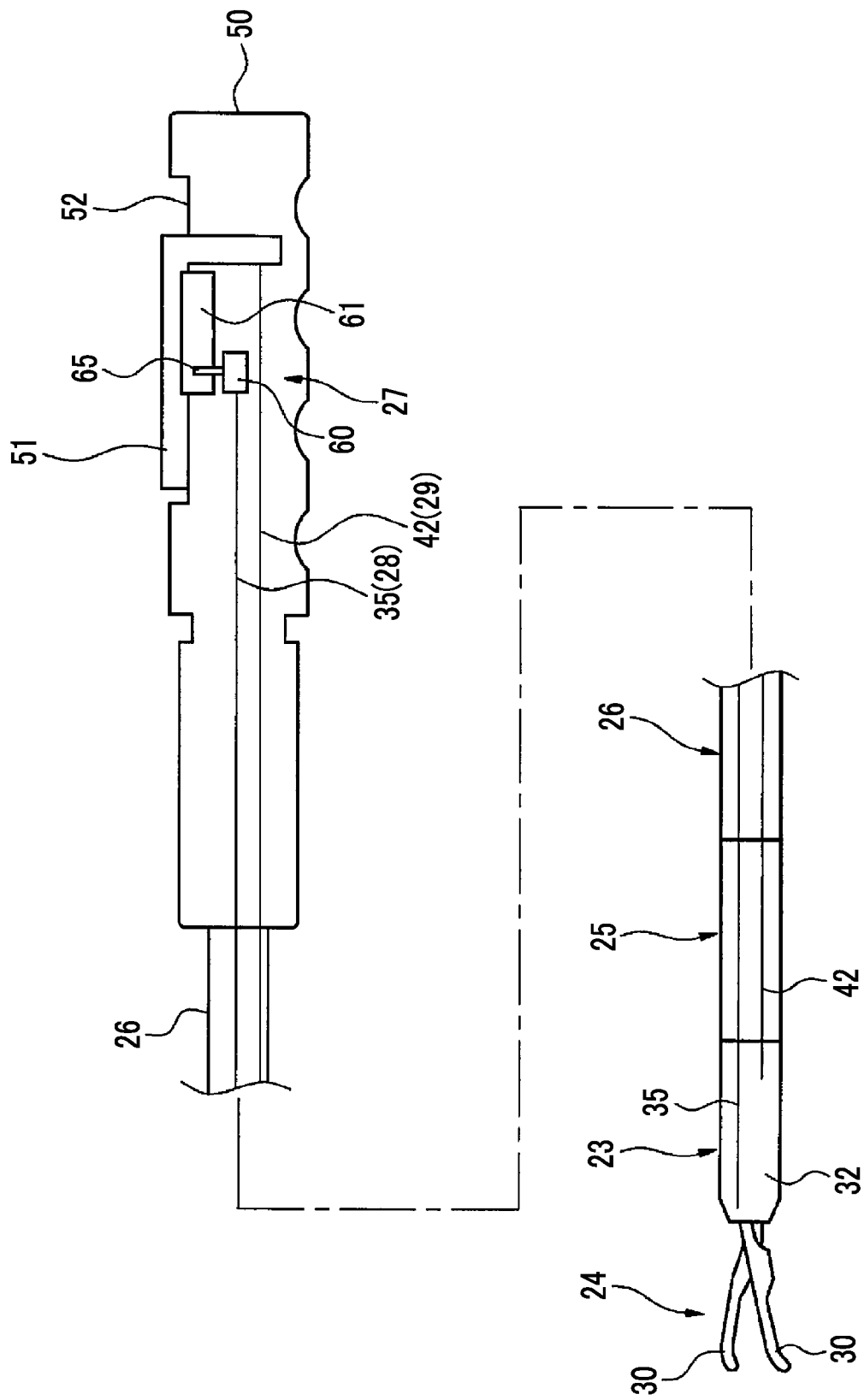
FIG. 10 is a view showing a transmitting part of the treatment tool for an endoscope of FIG. 2.
Figure 11:
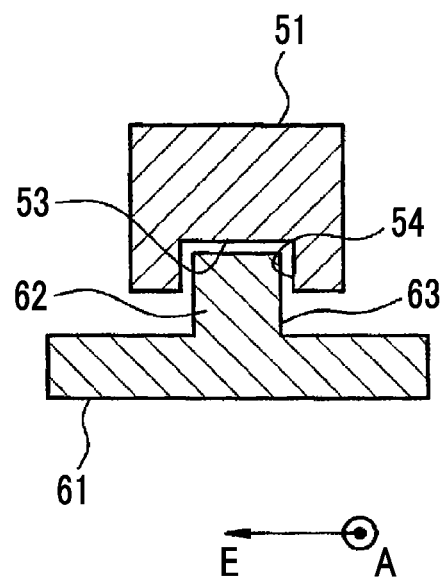
FIG. 11 is a view showing an engaging part of the transmitting part of FIG. 10.
Figure 12:
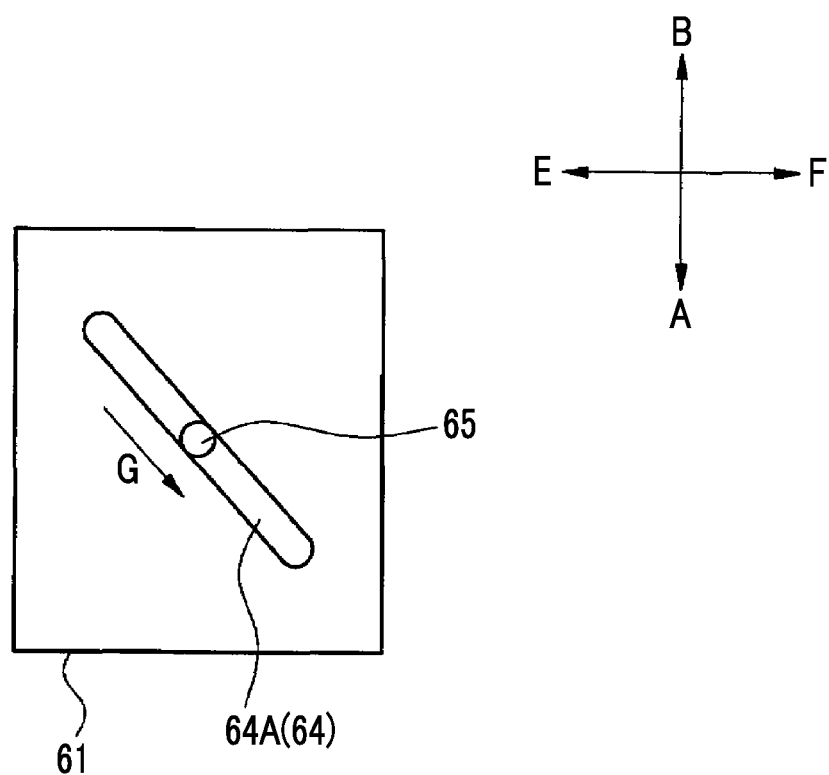
FIG. 12 is a view showing a cam groove of the transmitting part of FIG. 10.

FIG. 9 shows the operating part 22.

The operating part 22 has an operating part body 50 and an operating member 51. The operating part body 50 is formed in a cylindrical shape, and the soft portion 26 is connected to a distal end part of the operating part body 50 on one side in the axial direction. The wire 35 which is the first transmitting member 28 and the wire 42 which is the second transmitting member 29 are drawn inside the operating part body 50. A central axis of the operating part body 50 is disposed on an extension of the central axis of the insertion part 21 or is disposed parallel to the central axis of the insertion part 21, and extends in the A-direction (first direction), which is a moving direction of the wire 35 and the wire 42. A plane portion 52 parallel to the A-direction is provided on a part of an outer peripheral surface of the operating part body 50. The operating member 51 is provided on the plane portion 52, is movable in the A-direction along the plane portion 52, and is movable in an E-direction (second direction) perpendicular to the A-direction.

FIGS. 10 to 14 show the transmitting part 27.

The transmitting part 27 has a follower member 60 and a cam member 61. The follower member 60 and the cam member 61 are provided inside the operating part body 50. The follower member 60 is movable only in the axial direction of the operating part body 50, that is, the A-direction. On the other hand, the cam member 61 is movable only in the E-direction perpendicular to the A-direction, in a plane parallel to the plane portion 52 of the operating part body 50.

The cam member 61 has an engaging part 62, and the engaging part 62 extends in the A-direction. The operating member 51 is provided with an engaging part 53 that engages with the engaging part 62, and the engaging part 53 also extends in the A-direction. The engaging part 62 is formed in a convex shape in a cross section perpendicular to the A-direction, the engaging part 53 is formed in a concave shape in a cross section perpendicular to the A-direction, and a convex part of the engaging part 62 and a concave part of the engaging part 53 are fitted to each other. A side surface 63 of the convex part of the engaging part 62 and the side surface 54 of the concave part of the engaging part 53 extend in the A-direction and intersect the E-direction. The engaging part 62 may be formed in a concave shape, and the engaging part 53 may be formed in a convex shape.

Based on the engagement between the side surface 54 of the engaging part 53 and the side surface 63 of the engaging part 62, a relative movement in the A-direction between the operating member 51 and the cam member 61 is allowed, and a relative movement in the E-direction is prevented. That is, in response to an operation of the operating member 51 in the A-direction, the side surface (engaging surface) 54 of the engaging part 53 and the side surface (engaging surface) 63 of the engaging part 62 slide in the A-direction, a movement of the operating member 51 in the A-direction is not transmitted to the cam member 61, and the operating member 51 is independently moved in the A-direction. On the other hand, in response to an operation of the operating member 51 in the E-direction, the side surface (engaging surface) 54 of the engaging part 53 and the side surface (engaging surface) 63 of the engaging part 62 abut against each other, a movement of the operating member 51 in the E-direction is transmitted to the cam member 61, and the cam member 61 is moved in the E-direction integrally with the operating member 51.

In addition, the cam member 61 has a cam groove 64, and the follower member 60 has a cam pin 65. The cam pin 65 engages with the cam groove 64 so as to be movable in an extending direction of the cam groove 64. The cam groove 64 has a drive region 64A, and the drive region 64A extends in a G-direction (third direction) intersecting the A-direction and the E-direction, in a plane where the cam member 61 moves. In a case where the cam member 61 is moved in the E-direction, the cam pin 65 is moved in the drive region 64A in the G-direction, and the follower member 60 is moved in the A-direction in response to the movement of the cam pin 65.

Figure 13:
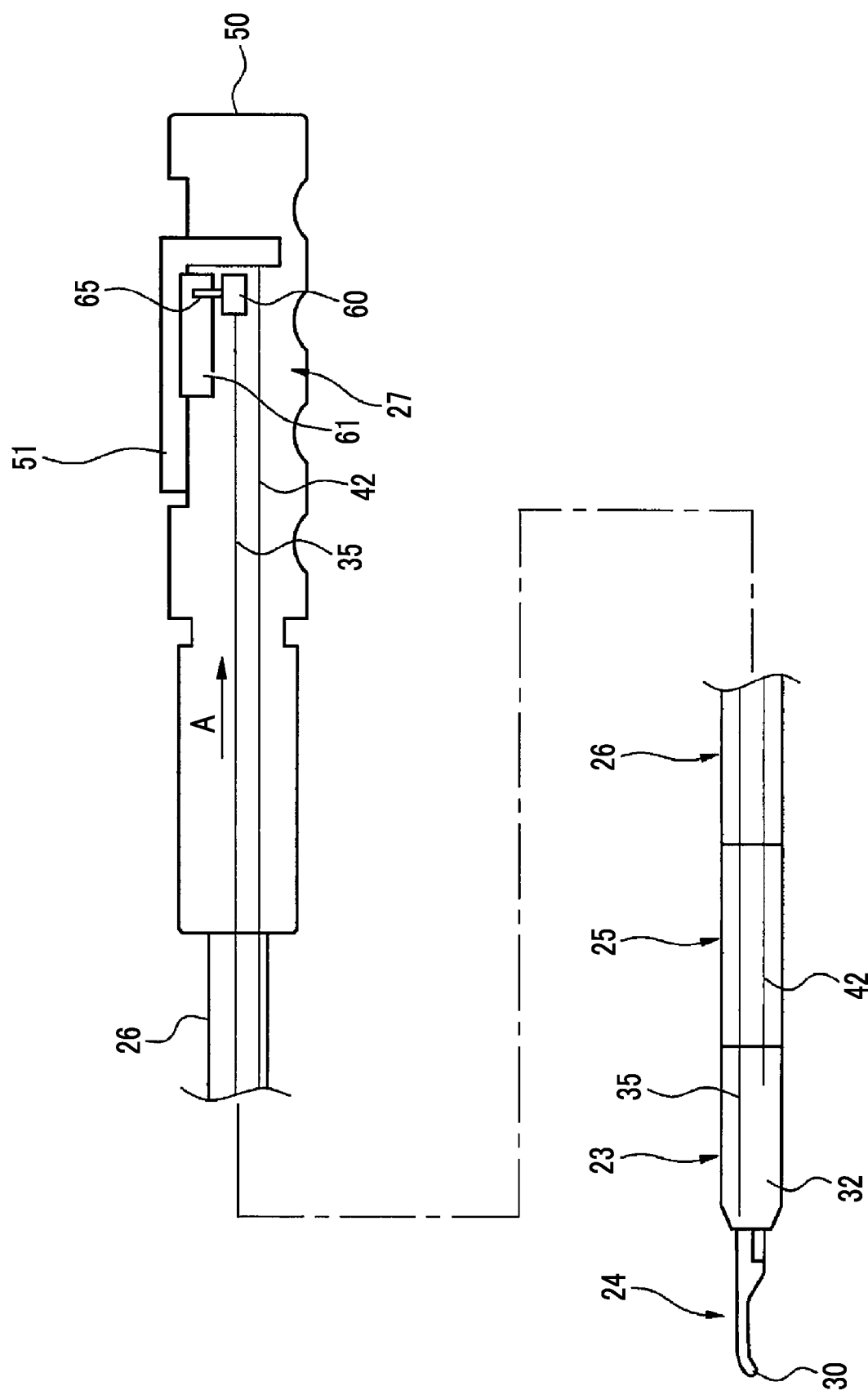
FIG. 13 is a view showing an operation of the transmitting part of FIG. 10.

The wire 35, which is the first transmitting member 28, is connected to the follower member 60, and the wire 42, which is the second transmitting member 29, is connected to the operating member 51. First, as shown in FIG. 13, the cam member 61 is moved in the E-direction in response to an operation of the operating member 51 in the E-direction, and the follower member 60 is moved in the A-direction in response to the movement of the cam member 61 in the E-direction. Accordingly, the wires 35 is moved in the A-direction, and the grip part 24 is closed. In a case where the grip part 24 is closed, the operating member 51 is operated only in the E-direction, and is not moved in the A-direction orthogonal thereto. The wire 42 connected to the operating member 51 is also not moved in the A-direction, and the bendable part 25 is maintained in a linear shape.

Figure 14:
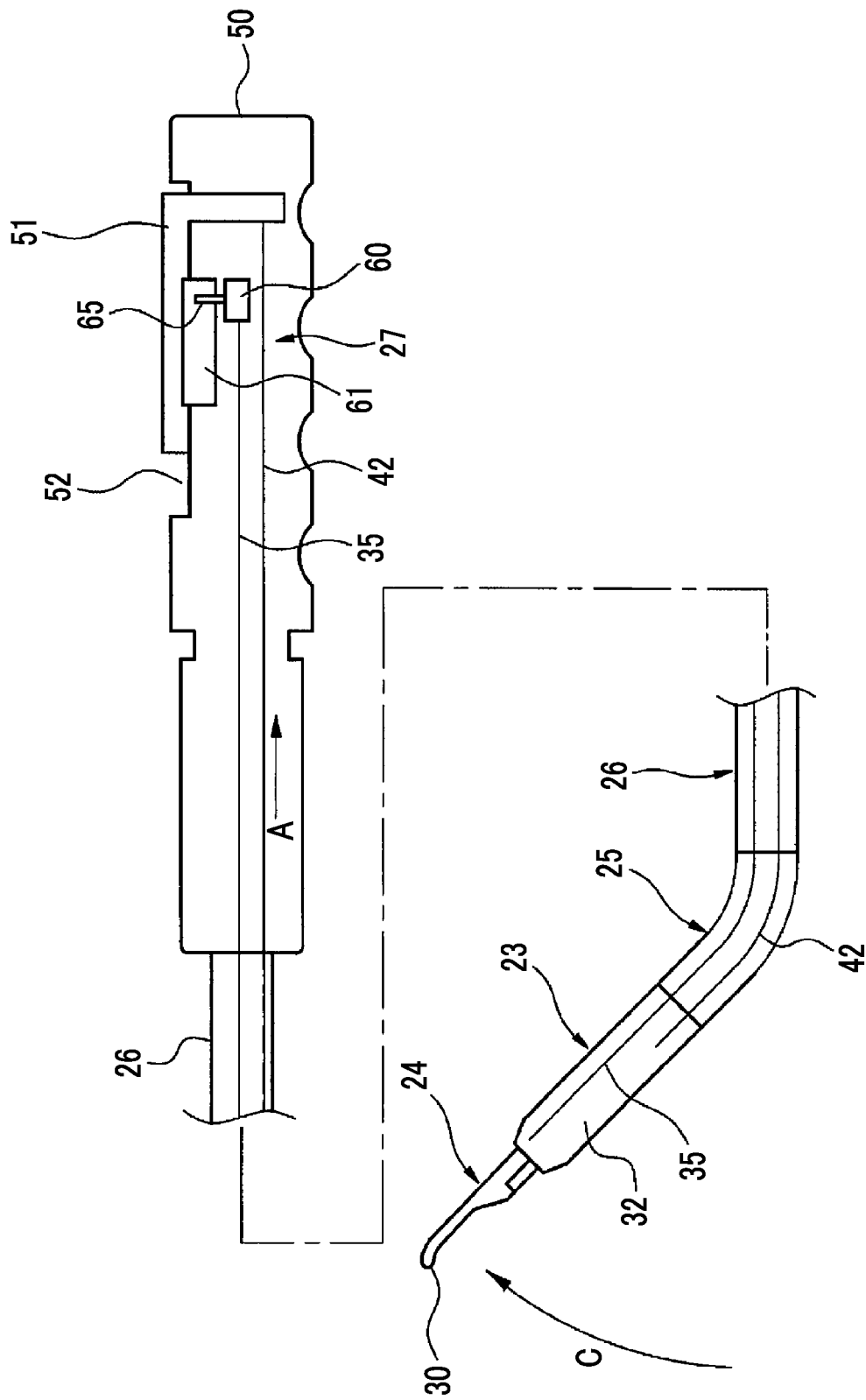
FIG. 14 is a view showing the operation of the transmitting part of FIG. 10.

Next, as shown in FIG. 14, the wire 42 is moved in the A-direction in response to an operation of the operating member 51 in the A-direction, and the bendable part 25 is bent as described above. In a case where the bendable part 25 is bent, the operating member 51 is operated in the A-direction, and is not moved in the E-direction orthogonal thereto. Therefore, the follower member 60 is not moved in the A-direction via the cam member 61, and the grip part 24 is maintained in a closed state.

Figure 15:
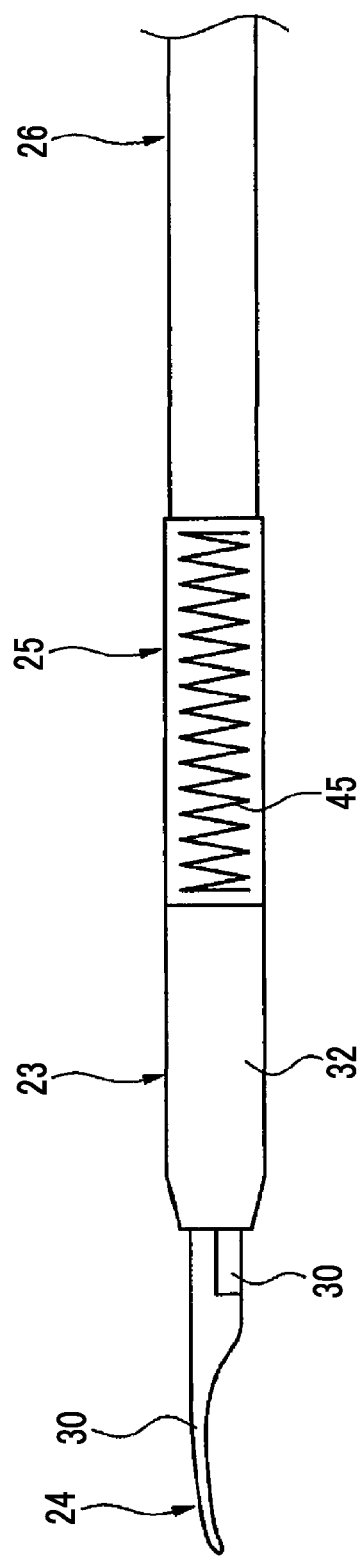
FIG. 15 is a view showing a modification example of the bendable part of the treatment tool for an endoscope of FIG. 2.

As the operating member 51 is moved in an F-direction opposite to the E-direction, the wire 35 connected to the operating member 51 is moved in the B-direction opposite to the A-direction, and the grip part 24 is opened. In addition, as the operating member 51 is moved in the B-direction opposite to the A-direction, the wire 42 is moved in the B-direction, and the bendable part 25 is restored to a linear shape. As shown in FIG. 15, in order to restore the bendable part 25 to a linear shape, an elastic member 45 such as a leaf spring and a coil spring may be provided at the bendable part 25.

As show in FIG. 16, a holding region 64B extending in the F-direction from one end of the drive region 64A on a G-direction side may be provided at the cam groove 64, and/or a holding region 64C extending in the E-direction from one end of the drive region 64A on an opposite side may be provided at the cam groove 64. In response to an operation of the operating member 51 in the E-direction, while the cam pin 65 is moved in the drive region 64A in the G-direction and the grip part 24 is closed, the holding region 64B can hold the grip part 24 in a completely closed state, and the holding region 64C can hold the grip part 24 in a completely open state. Further, a locking part 66 that locks the cam pin 65 which has entered the holding region 64B and the holding region 64C may be provided in the cam groove 64. The locking part 66 can be configured, for example, by a protrusion formed on the side surface of the cam groove 64.

In addition, the wire 35 for closing the grip part 24 may be connected to the operating member 51, and the wire 42 for bending the bendable part 25 may be connected to the follower member 60. In this case, the grip part 24 is closed as the operating member 51 is operated in the A-direction, and the bendable part 25 is bent as the operating member 51 is operated in the E-direction. The holding region 64B of the cam groove 64 can hold the bendable part 25 in a maximum bent state, and the holding region 64C can hold the bendable part 25 in a linear shape.

FIGS. 17 to 20 show another example of the operating part 22 and the transmitting part 27.

Figure 17:
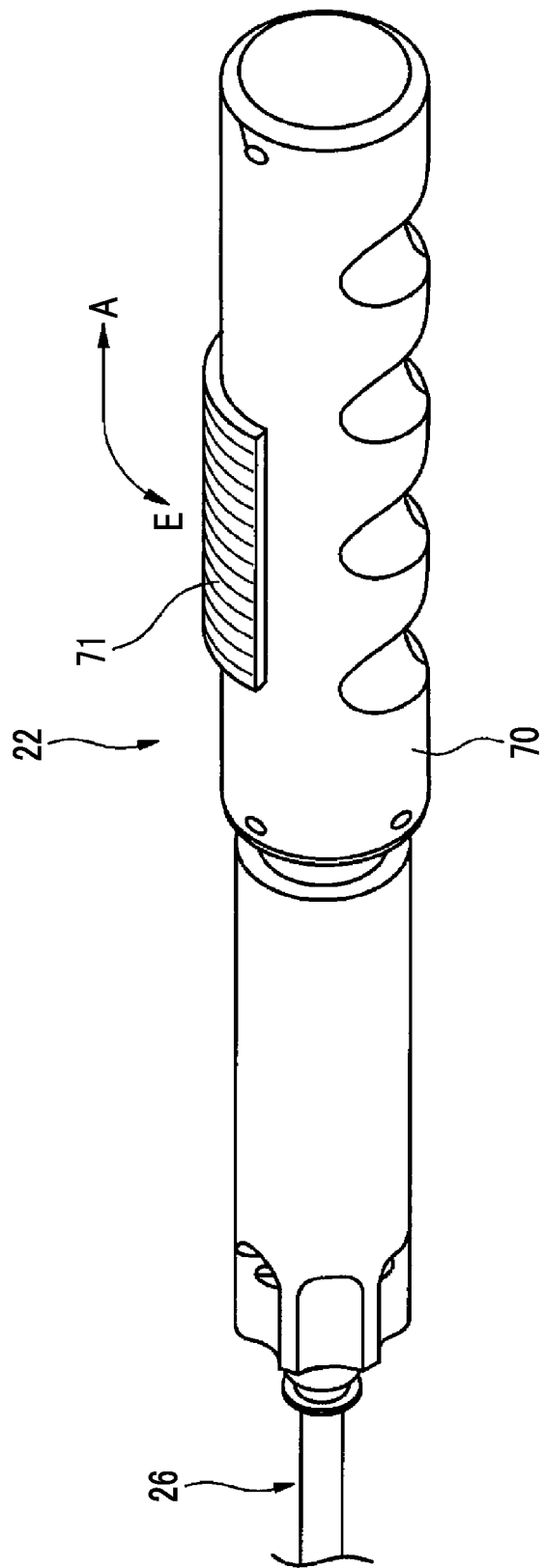
FIG. 17 is a view showing another example of the operating part of the treatment tool for an endoscope of FIG. 2.

The operating part 22 shown in FIG. 17 has an operating part body 70 and an operating member 71. The operating part body 70 is formed in a cylindrical shape, and the soft portion 26 is connected to a distal end part of the operating part body 70 on one side in the axial direction. The wire 35 which is the first transmitting member 28 and the wire 42 which is the second transmitting member 29 are drawn inside the operating part body 70, and a central axis of the operating part body 70 extends in the A-direction (first direction), which is the moving direction of the wire 35 and the wire 42. The operating member 71 is provided on an outer peripheral surface of the operating part body 70, is movable in the A-direction along the outer peripheral surface, and is movable in the E-direction (second direction) which is a circumferential direction of the outer peripheral surface.

Figure 18:
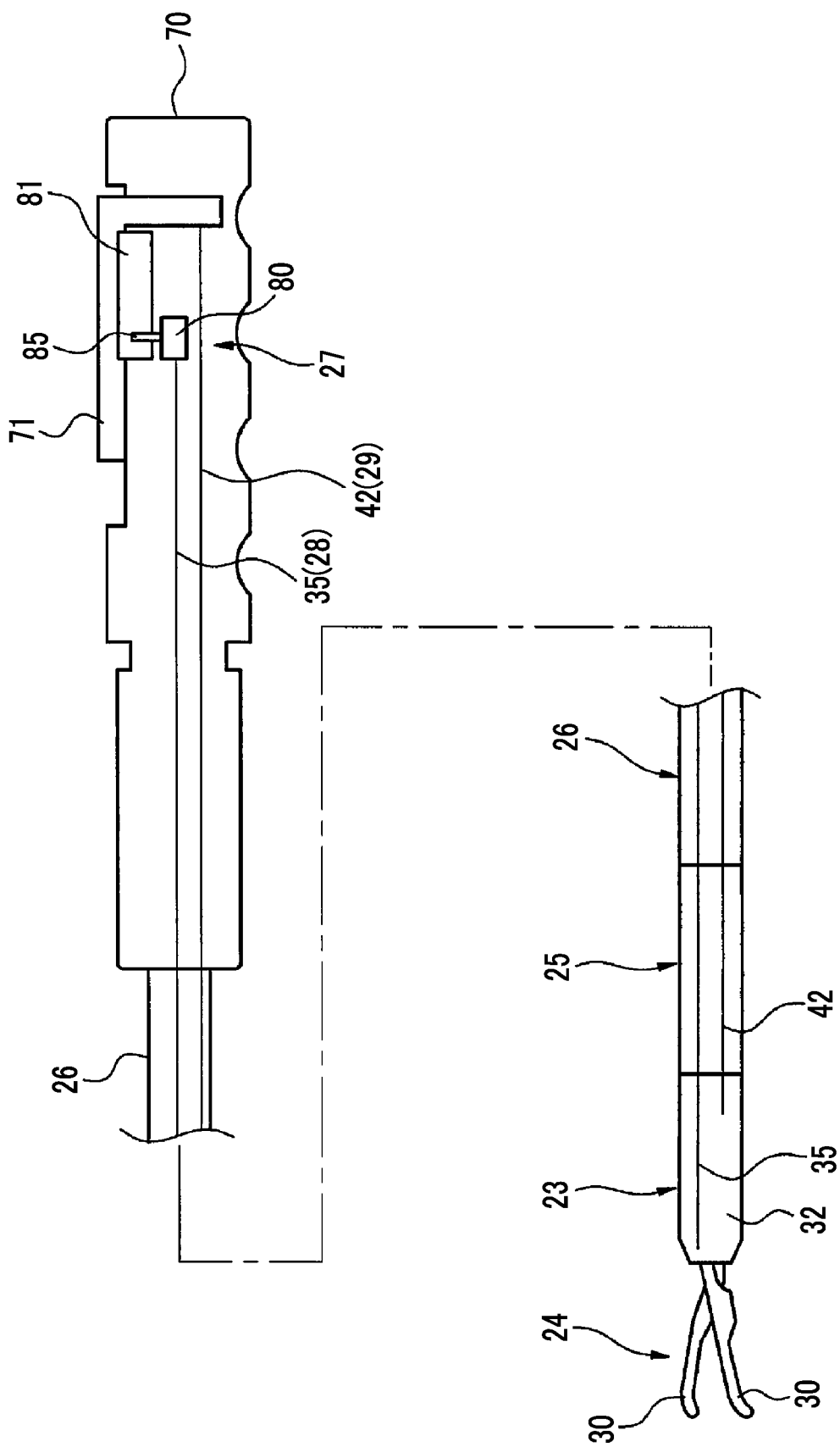
FIG. 18 is a view showing another example of the transmitting part of the treatment tool for an endoscope of FIG. 2.

The transmitting part 27 shown in FIGS. 18 to 20 has a follower member 80 and a cam member 81. The follower member 80 and the cam member 81 are provided inside the operating part body 70. The follower member 80 is movable only in the axial direction of the operating part body 70, that is, the A-direction. On the other hand, the cam member 81 is movable only in the E-direction which is a circumferential direction in a cylindrical plane coaxial with the outer peripheral surface of the operating part body 70.

The cam member 81 has an engaging part 82, and the engaging part 82 extends in the A-direction. The operating member 71 is provided with an engaging part 73 that engages with the engaging part 82, and the engaging part 73 also extends in the A-direction. The engaging part 82 is formed in a convex shape in a cross section perpendicular to the A-direction, the engaging part 73 is formed in a concave shape in a cross section perpendicular to the A-direction, and a convex part of the engaging part 82 and a concave part of the engaging part 73 are fitted to each other. A side surface 83 of the convex part of the engaging part 82 and a side surface 74 of the concave part of the engaging part 73 extend in the A-direction and intersect the E-direction. The engaging part 82 may be formed in a concave shape, and the engaging part 73 may be formed in a convex shape.

Based on the engagement between the side surface 74 of the engaging part 73 and the side surface 83 of the engaging part 82, a relative movement in the A-direction between the operating member 71 and the cam member 81 is allowed, and a relative movement in the E-direction is prevented. That is, in response to an operation of the operating member 71 in the A-direction, the side surface (engaging surface) 74 of the engaging part 73 and the side surface (engaging surface) 83 of the engaging part 82 slide in the A-direction, a movement of the operating member 71 in the A-direction is not transmitted to the cam member 81, and the operating member 71 is independently moved in the A-direction. On the other hand, in response to an operation of the operating member 71 in the E-direction, the side surface (engaging surface) 74 of the engaging part 73 and the side surface (engaging surface) 83 of the engaging part 82 abut against each other, a movement of the operating member 71 in the E-direction is transmitted to the cam member 81, and the cam member 81 is moved in the E-direction integrally with the operating member 71.

In addition, the cam member 81 has a cam groove 84, and the follower member 80 has a cam pin 85. The cam pin 85 engages with the cam groove 84 so as to be movable in an extending direction of the cam groove 84. The cam groove 84 has a drive region 84A, and the drive region 84A extends in the G-direction (third direction) intersecting the A-direction and the E-direction, in a cylindrical plane where the cam member 81 moves. In a case where the cam member 81 is moved in the E-direction, the cam pin 85 is moved in the drive region 84A in the G-direction, and the follower member 80 is moved in the A-direction in response to the movement of the cam pin 85.

The wire 35, which is the first transmitting member 28, is connected to the follower member 80, and the wire 42, which is the second transmitting member 29, is connected to the operating member 71. As described above, the cam member 81 is moved in the E-direction in response to an operation of the operating member 71 in the E-direction, and the follower member 80 is moved in the A-direction in response to the movement of the cam member 81 in the E-direction. Accordingly, the wires 35 is moved in the A-direction, and the grip part 24 is closed. In a case where the grip part 24 is closed, the operating member 71 is operated in the E-direction, and is not moved in the A-direction orthogonal thereto. The wire 42 connected to the operating member 71 is also not moved in the A-direction, and the bendable part 25 is maintained in a linear shape.

Next, in response to an operation of the operating member 71 in the A-direction, the wire 42 is moved in the A-direction, and the bendable part 25 is bent as described above. In a case where the bendable part 25 is bent, the operating member 71 is operated in the A-direction, and is not moved in the E-direction orthogonal thereto. Therefore, the follower member 80 is not moved in the A-direction via the cam member 81, and the grip part 24 is maintained in a closed state.

The wire 35 for closing the grip part 24 may be connected to the operating member 71, and the wire 42 for bending the bendable part 25 may be connected to the follower member 80. In this case, the grip part 24 is closed as the operating member 71 is operated in the A-direction, and the bendable part 25 is bent as the operating member 71 is operated in the E-direction.

FIGS. 21 to 24 show a treatment method for ESD as an example of a treatment method using the treatment tool for an endoscope 20.

Figure 21:
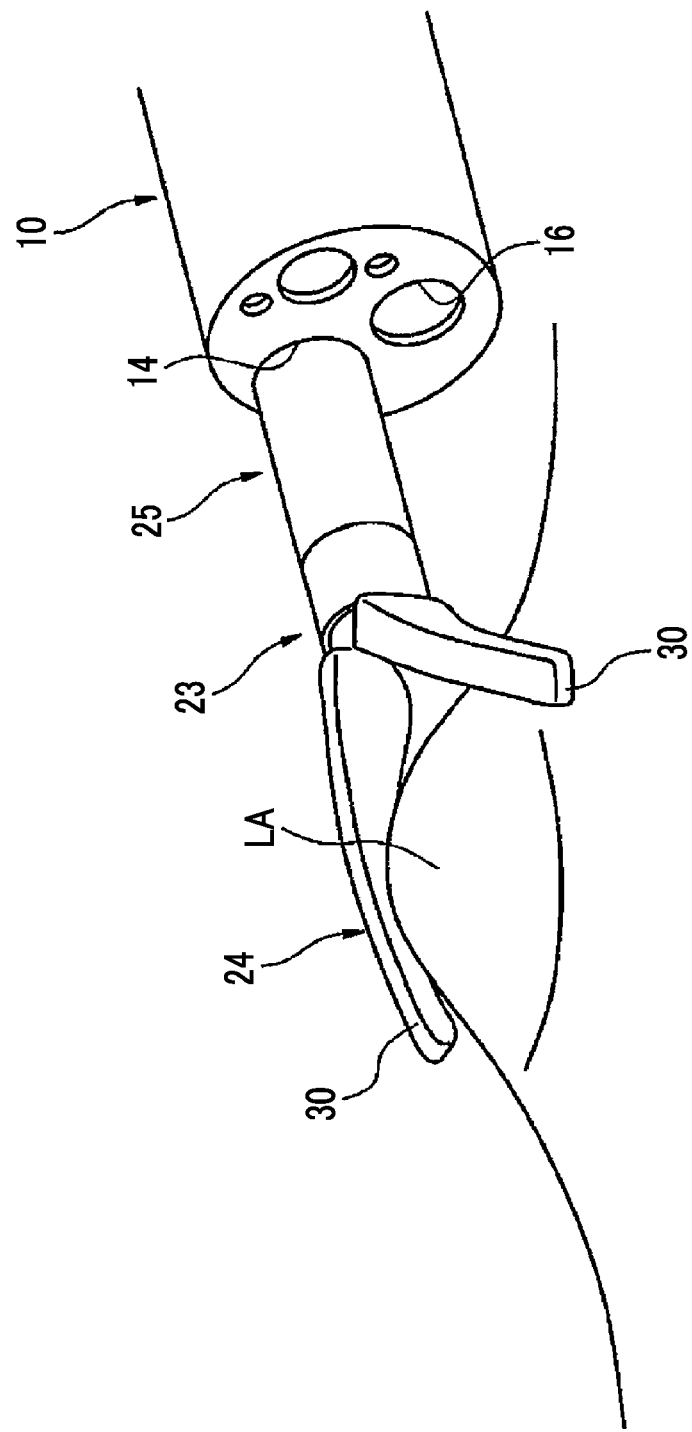
FIG. 21 is a view showing an example of a treatment method using a combination of the treatment tool for an endoscope of FIG. 2 and another endoscope treatment tool.

The endoscope 2 is inserted into the body, and the endoscope distal end part 10 is disposed at the side of a lesion part LA of a mucous membrane layer. The treatment tool for an endoscope 20 is inserted into the first treatment tool channel 14 of the endoscope 2, and the distal end part 23 and the bendable part 25 of the treatment tool for an endoscope 20 protrude from the edge surface of the endoscope distal end part 10 as shown in FIG. 21.

Figure 22:
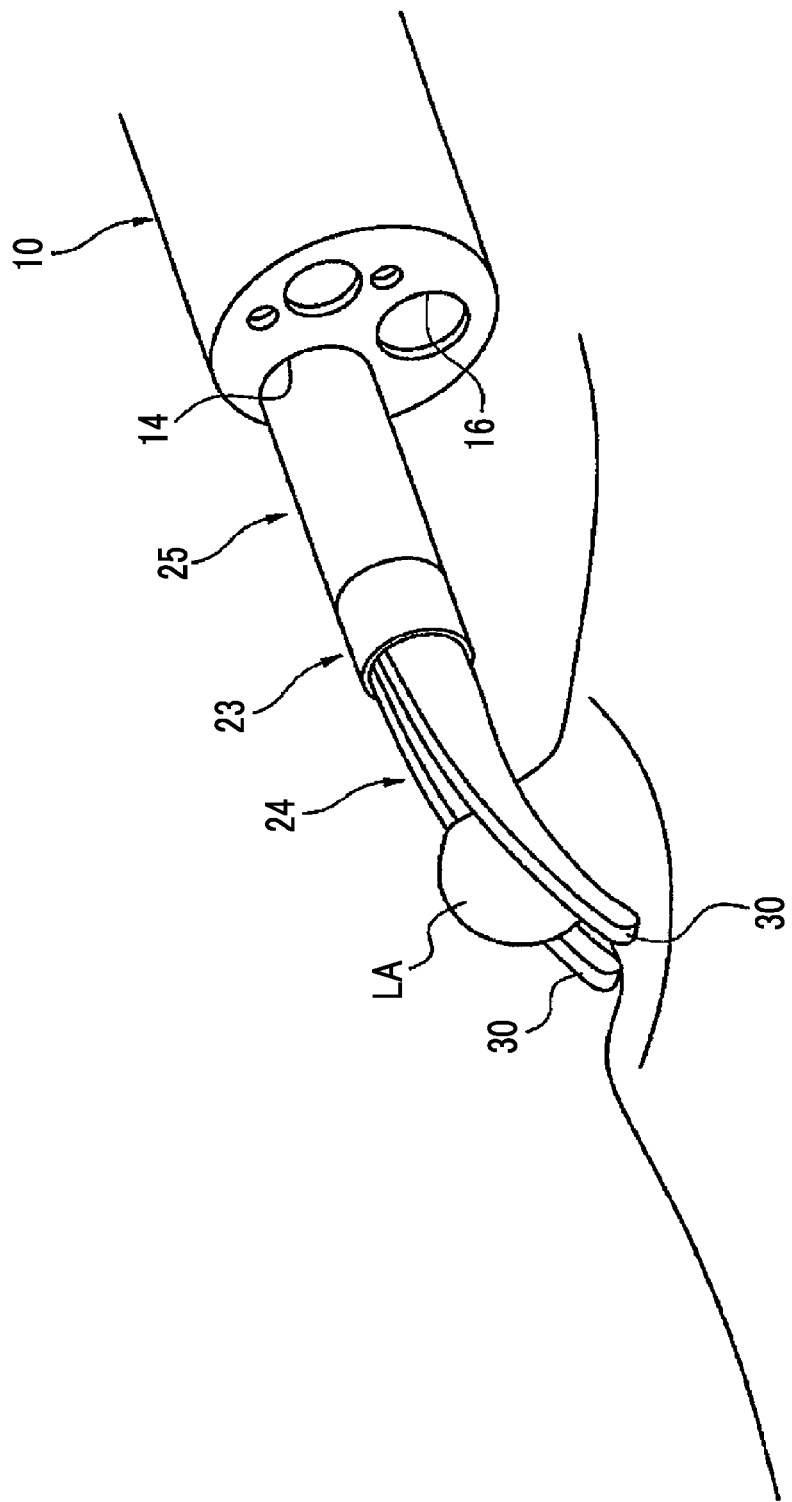
FIG. 22 is a view showing an example of the treatment method using the combination of the treatment tool for an endoscope of FIG. 2 and the other endoscope treatment tool.
Figure 23:
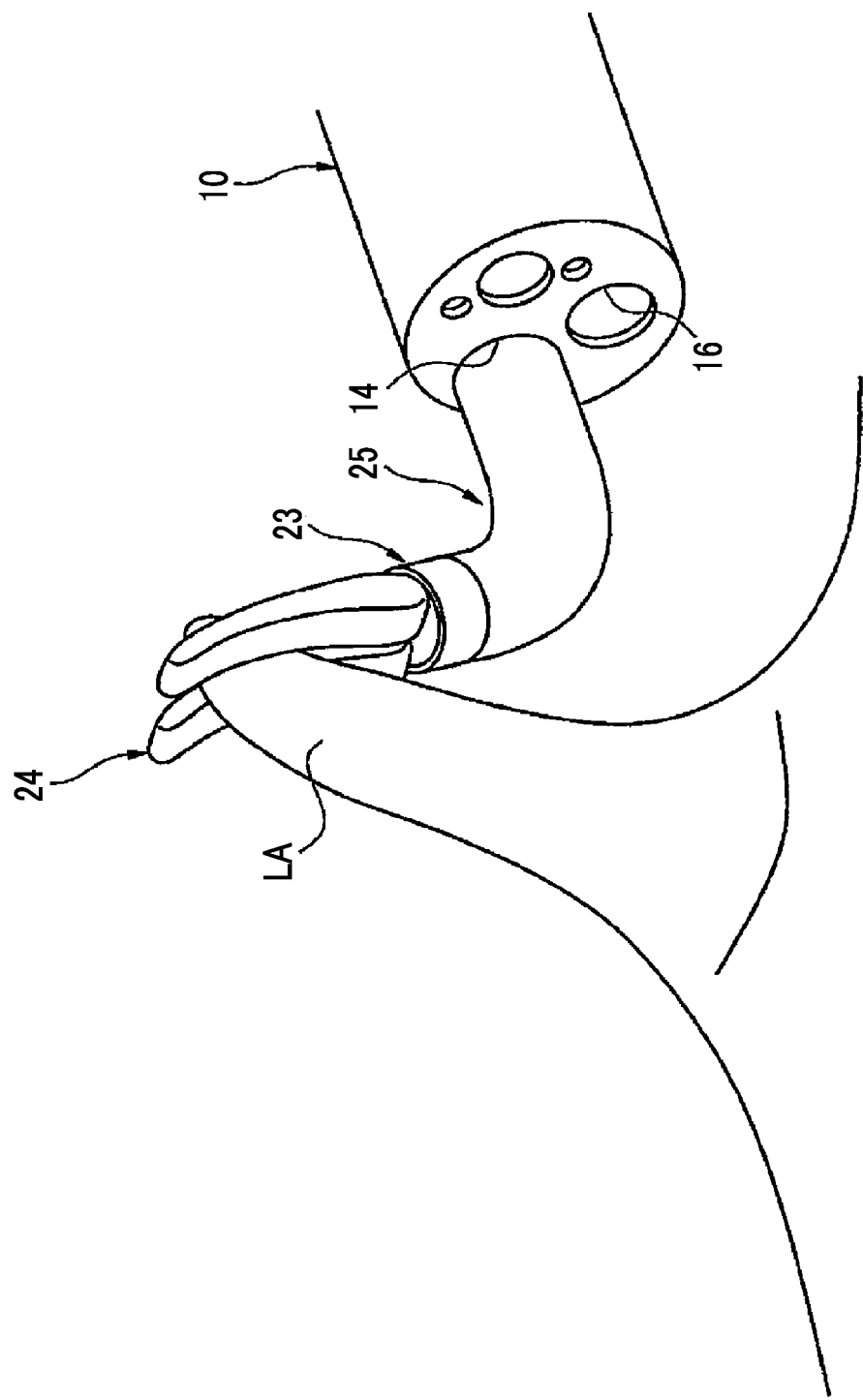
FIG. 23 is a view showing an example of the treatment method using the combination of the treatment tool for an endoscope of FIG. 2 and the other endoscope treatment tool.

Next, as shown in FIG. 22, the grip part 24 is closed based on an operation of the operating part 22, and the lesion part LA is gripped by the grip part 24. Then, after the lesion part LA is gripped by the grip part 24, the bendable part 25 is bent based on an operation of the operating part 22 as shown in FIG. 23. Accordingly, the grip part 24 is erected, and the lesion part LA gripped by the grip part 24 is lifted.

Figure 24:
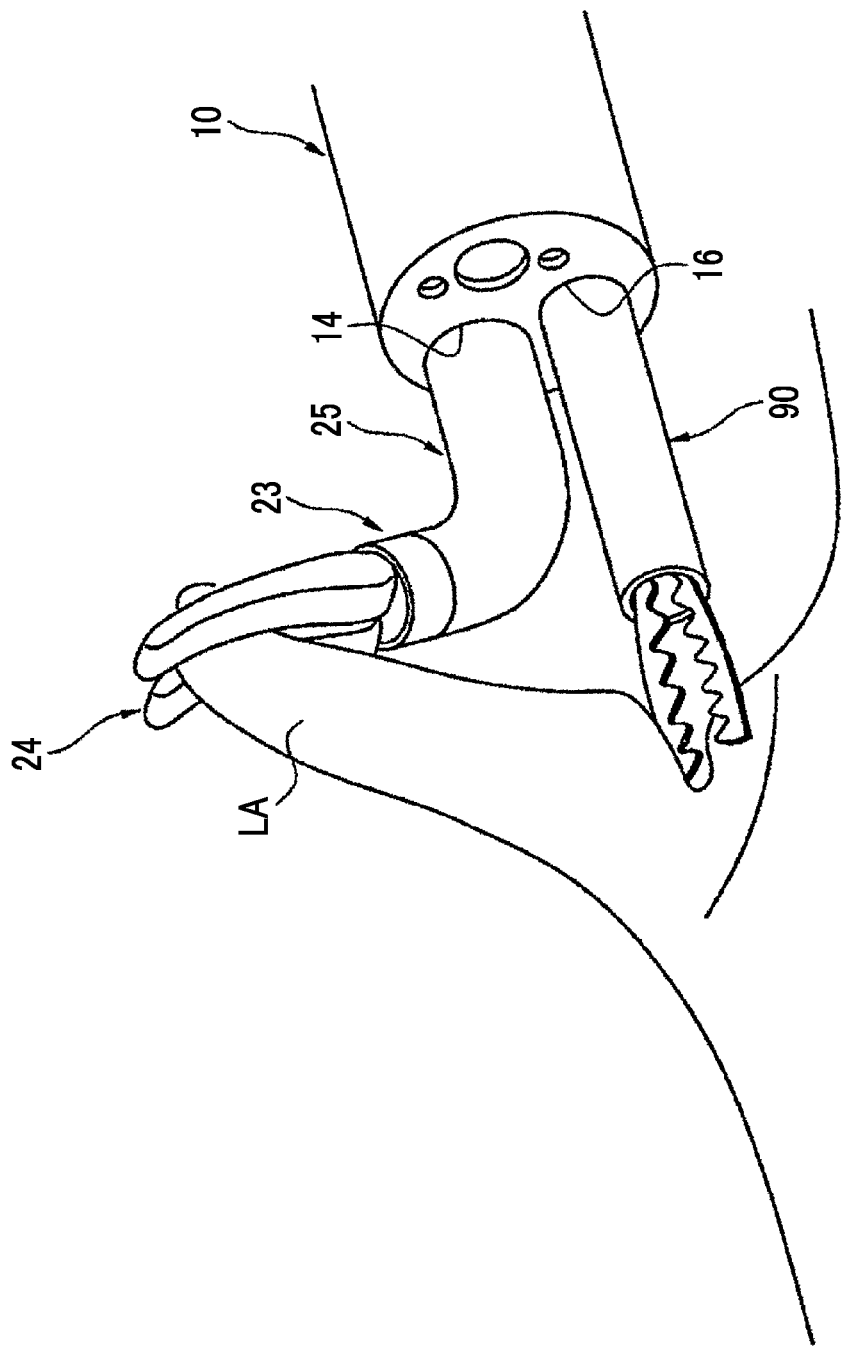
FIG. 24 is a view showing an example of the treatment method using the combination of the treatment tool for an endoscope of FIG. 2 and the other endoscope treatment tool.

In a state where the lesion part LA is being lifted, a high-frequency forcep 90 is inserted into the second treatment tool channel 16 of the endoscope 2, and the high-frequency forcep 90 protrudes from the edge surface of the endoscope distal end part 10 as shown in FIG. 24. Then, a lower part of the lesion part LA is incised by the high-frequency forcep 90.

The other endoscope treatment tool used in combination with the treatment tool for an endoscope 20 is selected as appropriate according to treatment, and is not limited to the high-frequency forcep 90. Examples of the other endoscope treatment tool include incision tools, such as high-frequency forceps and high-frequency knives, hemostatic tools, such as bipolar hemostatic forceps and clips, injection needles, and collection nets.

In the treatment method described above, the gripping of the lesion part LA by closing the grip part 24 and the lifting of the lesion part LA by bending the bendable part 25 are performed only with an operation of the operating member 51 or the operating member 71 of the operating part 22 as described above. A closing operation of closing the grip part 24 and a bending operation of bending the bendable part 25 are independent of each other, and in a case where the grip part 24 is closed, the bendable part 25 is maintained in a linear shape, and a relative movement between the grip part 24 and the lesion part LA is prevented. Accordingly, the gripping of the lesion part LA and the lifting of the gripped lesion part LA can be easily performed with an operation of the treatment tool for an endoscope 20 alone.

Herein, although it has been described that the wire 35 for closing the grip part 24 and the wire 42 for bending the bendable part 25 are disposed on the bent inner diameter side in the bending of the bendable part 25 in the C-direction, the wire 35 may be disposed on the bent outer diameter side in the bending of the bendable part 25 in the C-direction, or may be disposed on the bent neutral plane S of the bendable part 25.

The wire 35 for closing the grip part 24 is moved in the same A-direction as the wire 42 for bending the bendable part 25. In this case, friction can occur between the wire 35 and the bendable part 25. In a case where the wire 35 is disposed on the same bent inner diameter side of the bendable part 25 as the wire 42, there is a possibility that the bendable part 25 is bent in the C-direction due to the friction of the wire 35 and the grip part 24 which is closed to grip the lesion part LA is separated from the lesion part LA.

On the contrary, in a case where the wire 35 is disposed on the bent outer diameter side in the bending of the bendable part 25 in the C-direction, the grip part 24 is pressed against the lesion part LA as the bendable part 25 is bent in the D-direction opposite to the C-direction even though the bendable part 25 is bent due to the friction of the wire 35. In addition, in a case where the wire 35 is disposed on the bent neutral plane S of the bendable part 25, the bending of the bendable part 25 caused by the friction of the wire 35 is further prevented.

Further, the bendable part 25 may be configured to be not bendable in the D-direction. In this case, the bending of the bendable part 25 caused by the friction of the wire 35 is reliably prevented.

Figure 25:
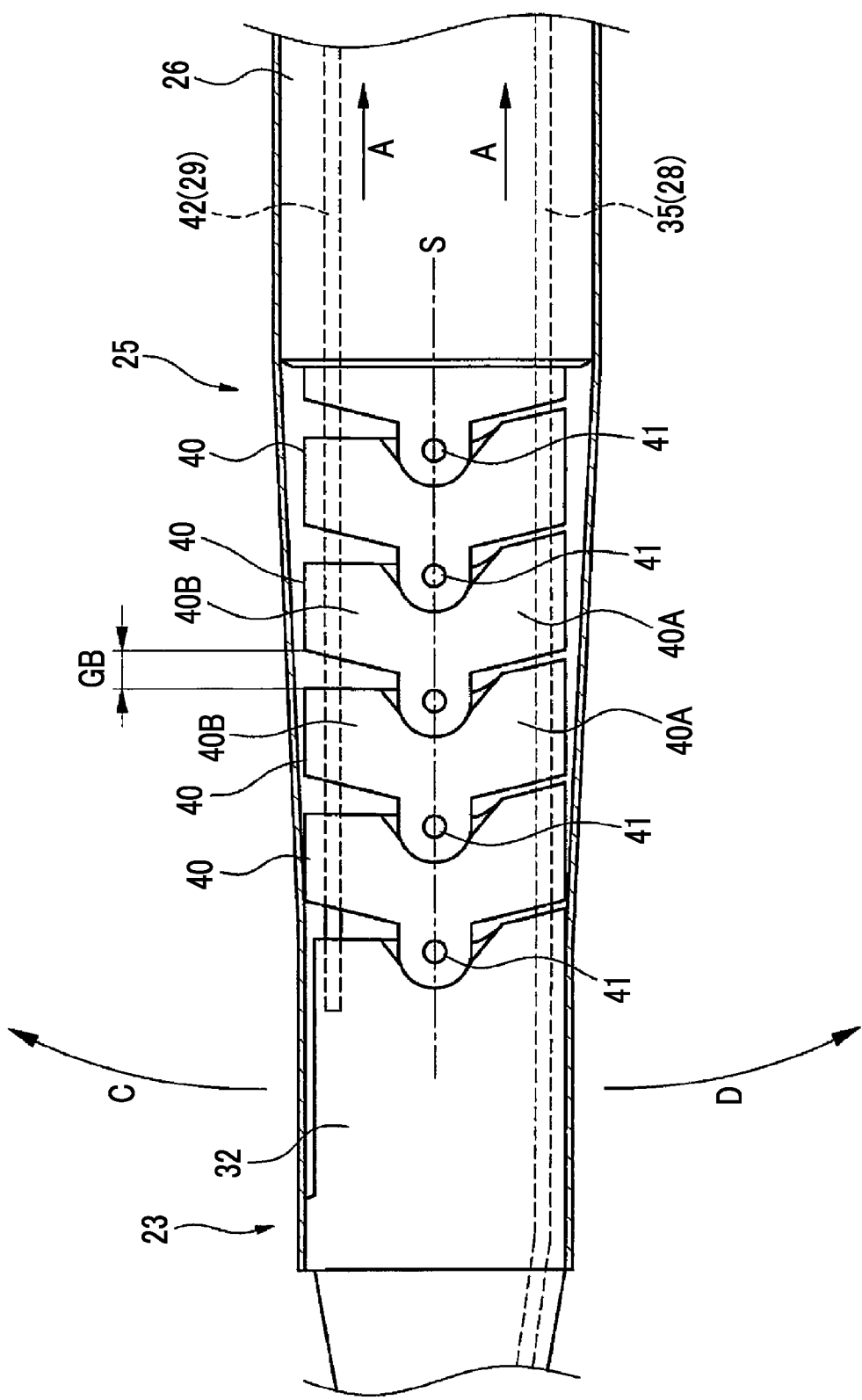
FIG. 25 is a view showing a modification example of the bendable part of FIG. 6.
Figure 26:
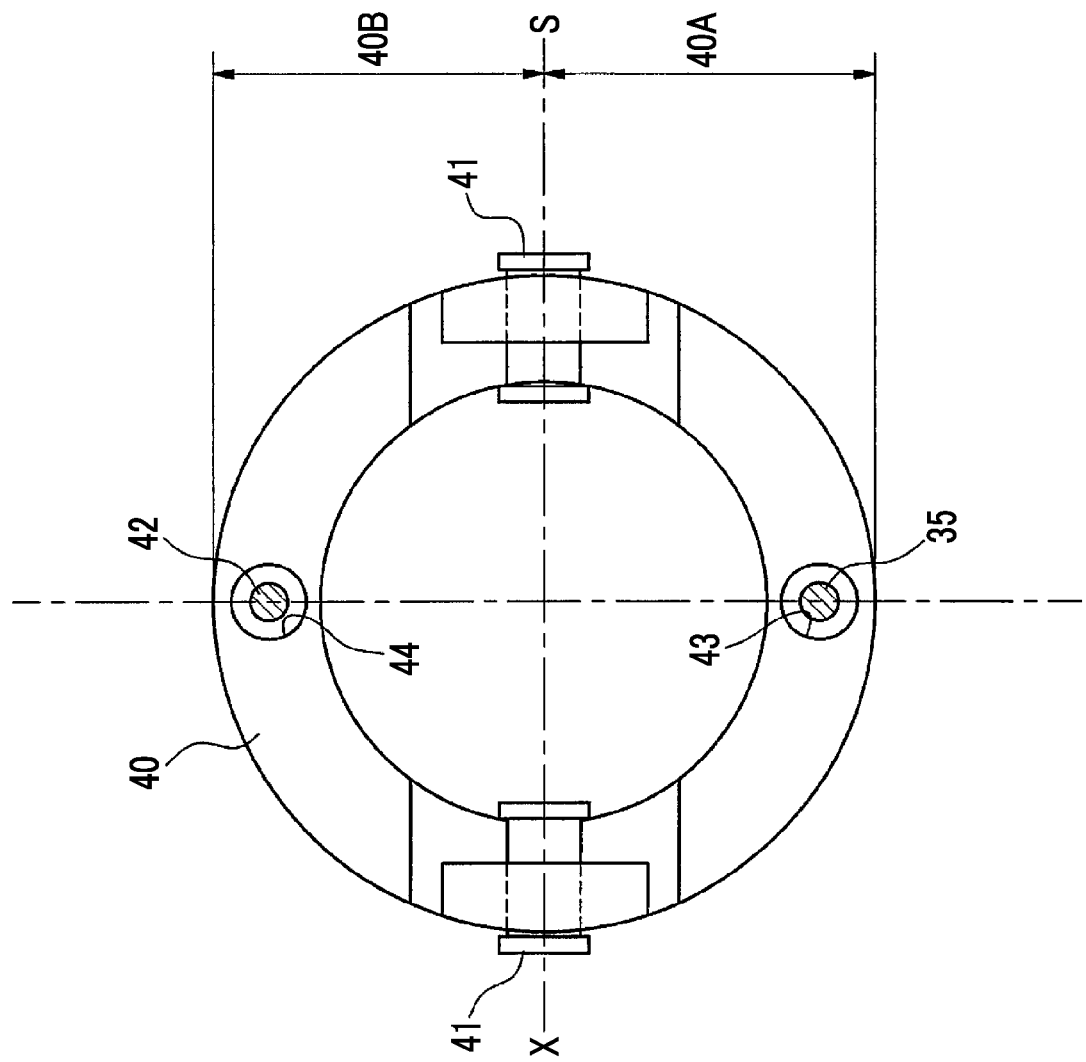
FIG. 26 is a view showing a cross section of the bendable part of FIG. 22.

In a case where the cyclic member 40 is divided into the first portion 40A and the second portion 40B with the bent neutral plane S of the bendable part 25 as a boundary in the bendable part 25 shown in FIGS. 25 and 26, the second portions 40B of the two cyclic members 40 adjacent to each other are contactless with the gap GB therebetween, but the first portions 40A are in contact with each other. Therefore, the bendable part 25 is bendable only in the C-direction, in which the gap GB is narrowed, and is not bendable in the D-direction opposite to the C-direction.

In the bending of the bendable part 25 in the C-direction, the first portion 40A of the cyclic member 40 is positioned on a bent outer diameter side, and the second portion 40B is positioned on a bent inner diameter side. The first guide 43 that holds the wire 35 which is the first transmitting member 28 is provided at the first portion 40A, and the wire 35 is disposed on the bent outer diameter side. The second guide 44 that holds the wire 42 which is the second transmitting member 29 is provided at the second portion 40B, and the wire 42 is disposed on the bent inner diameter side.

The gap GB is narrowed as the wire 42 is moved in the A-direction, and thus the bendable part 25 is bent in the C-direction. In a case where the wire 35 is disposed on the bent outer diameter side which is an opposite side to the wire 42 with the bent neutral plane S interposed therebetween and a bendable part 25 is bent due to the friction of the wire 35 moved in the A-direction, the bendable part 25 is bent in the D-direction opposite to the C-direction, but the bendable part 25 is not bendable in the D-direction. Therefore, based on an operation of the operating part 22, the wire 35 is moved in the A-direction, and in a case where the grip part 24 is closed, the bendable part 25 is reliably maintained in a linear shape. Accordingly, a relative movement between the grip part 24 and the lesion part LA gripped by the grip part 24 is prevented, and the gripping of the lesion part LA becomes even easier.

The wire 35 may be disposed on the bent neutral plane S. In a case where the wire 35 is disposed on the bent neutral plane S, the first guide 43 holding the wire 35 is provided, for example, at an end part of the pin 41.

Figure 27:
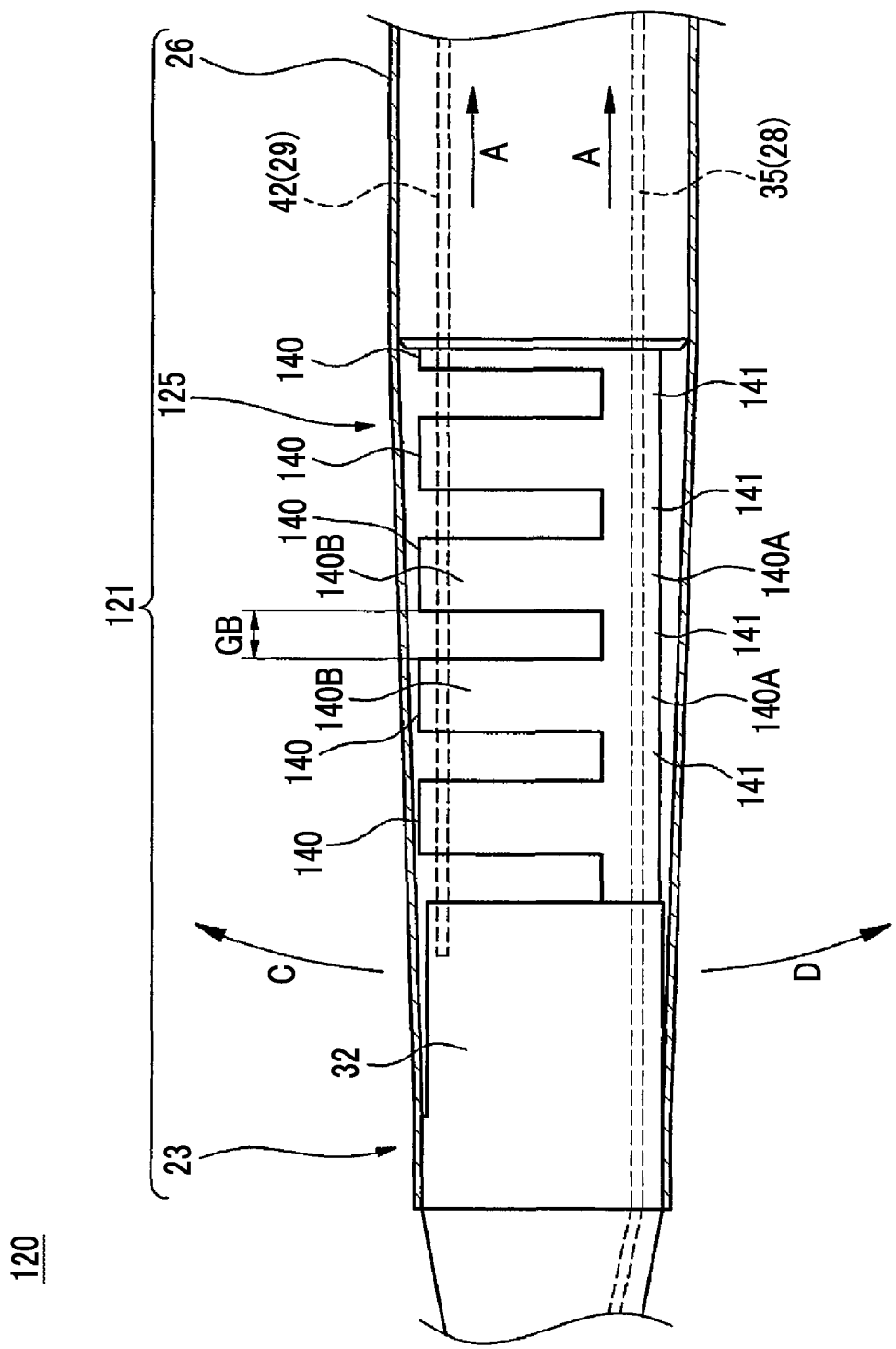
FIG. 27 is a view showing another example of the bendable part of the treatment tool for an endoscope, which is for describing Embodiment 1 of the present invention.
Figure 28:
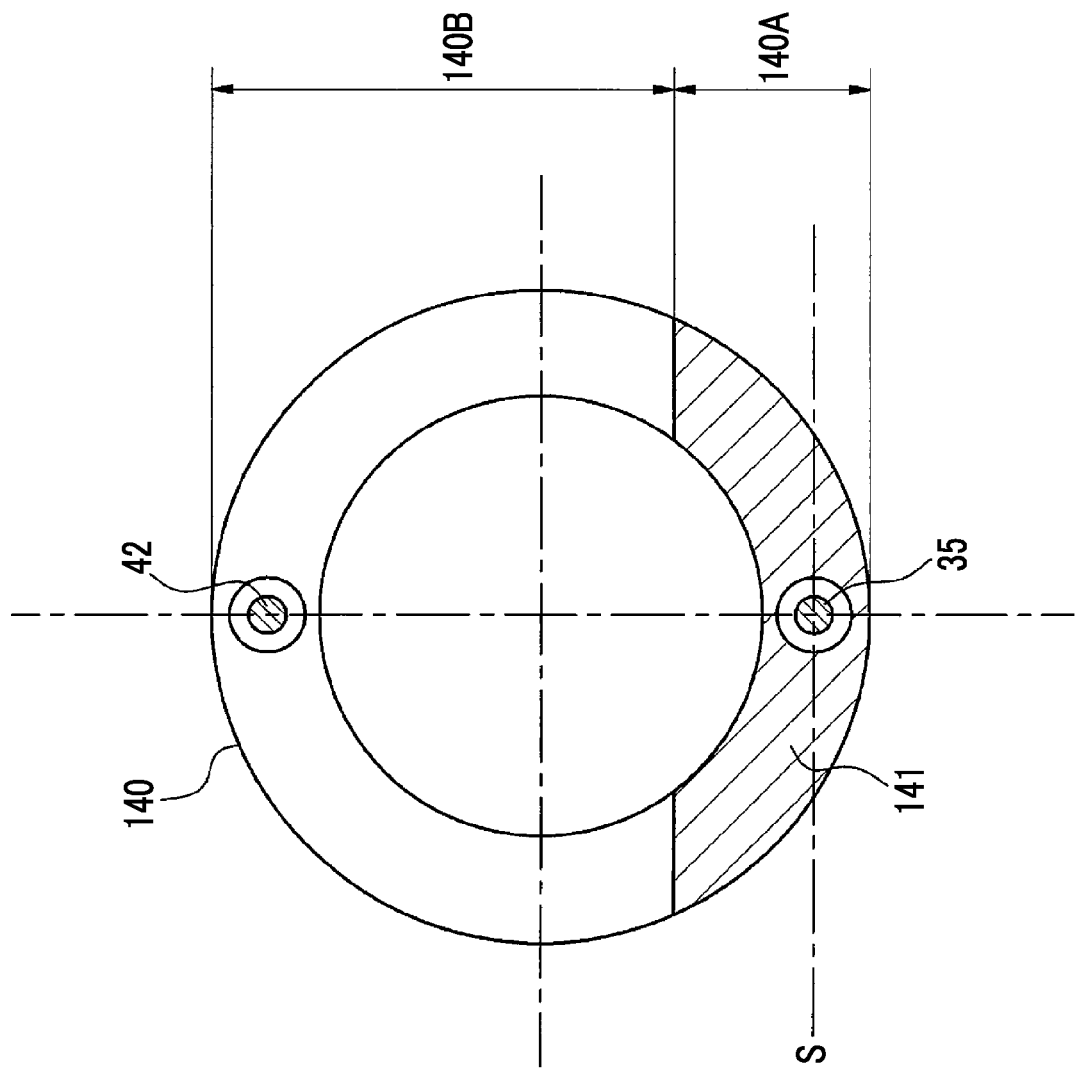
FIG. 28 is a view showing a cross section of the bendable part of FIG. 27.

A treatment tool for an endoscope 120 shown in FIGS. 27 and 28 is also configured such that the bendable part is bendable in one direction and is not bendable in an opposite direction. The treatment tool for an endoscope 120 and the treatment tool for an endoscope 20 described above are different from each other only in terms of the configuration of the bendable part. Thus, common elements will be assigned with common reference numerals, and description thereof will be omitted.

An insertion part 121 of the treatment tool for an endoscope 120 comprises the distal end part 23, the bendable part 125, and the soft portion 26. The bendable part 125 has a plurality of cyclic portions 140 arranged in an axial direction of the insertion part 121 and one or more connecting portions 141 that connect two cyclic portions 140 adjacent to each other. The cyclic portions 140 and the connecting portions 141 are formed integrally with each other. In a cross section perpendicular to the axial direction of the insertion part 121, the connecting portions 141 are formed in an arc shape that is concave to a central axis side of the insertion part 121.

In a case where the cyclic portion 140 is divided into a first portion 140A connected to the connecting portion 141 and a second portion 140B excluding the first portion 140A, there is the gap GB between the second portions 140B of the two cyclic portions 140 adjacent to each other. The connecting portion 141 having an arc-shaped cross section is capable of only bending a concave surface inward of bending the concave surface inward and bending the concave surface outward. Therefore, the bendable part 125 is bendable only in the C-direction, in which the gap GB is narrowed, with the bending of the concave surface of the connecting portion 141 inward, and is not bendable in the D-direction opposite to the C-direction. The bent neutral plane S of the bendable part 125 passes through a circumferential middle portion of each of the plurality of connecting portions 141 arranged in the axial direction of the insertion part 121.

The wire 42 which is the second transmitting member 29 is disposed on the bent inner diameter side in the bending of the bendable part 125 in the C-direction. The gap GB is narrowed as the wire 42 is moved in the A-direction, and thus the bendable part 125 is bent in the C-direction. The wire 35 which is the first transmitting member 28 is disposed on the bent neutral plane S of the bendable part 125. Since the bendable part 125 is not bendable in the D-direction opposite to the C-direction, based on an operation of the operating part 22, the wire 35 is moved in the A-direction, and in a case where the grip part 24 is closed, the bendable part 125 is reliably maintained in a linear shape. Accordingly, a relative movement between the grip part 24 and the lesion part LA gripped by the grip part 24 is prevented, and the gripping of the lesion part LA becomes even easier.

Figure 29:
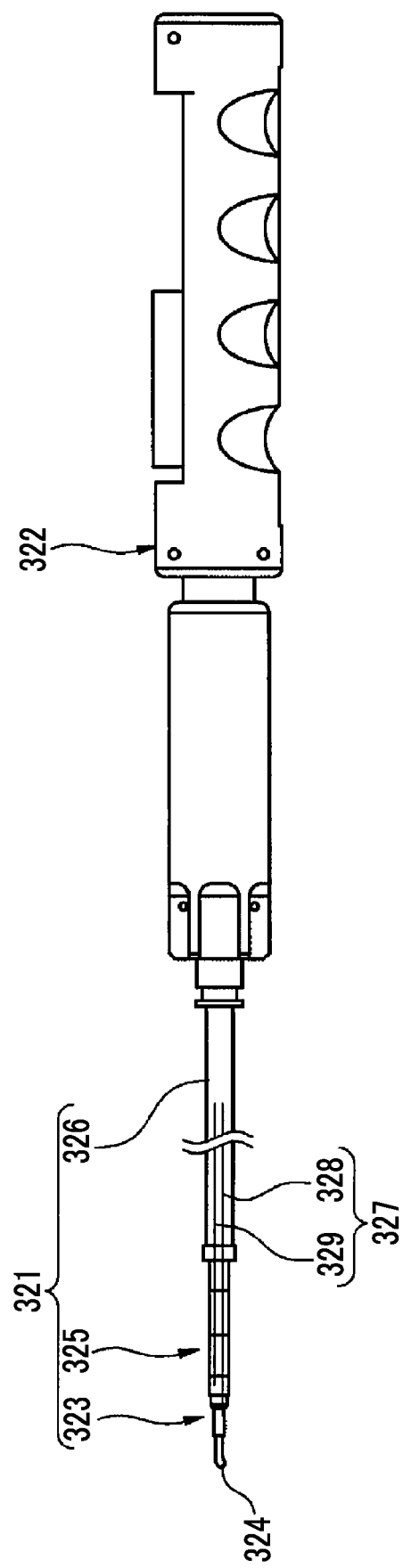
FIG. 29 is a view showing another example of the treatment tool for an endoscope, which is for describing Embodiment 1 of the present invention.

FIG. 29 shows another example of the treatment tool for an endoscope, which is for describing Embodiment 1 of the present invention.

A treatment tool for an endoscope 320 comprises an insertion part 321 and an operating part 322. The insertion part 321 has a distal end part 323 at which an openable and closable grip part 324 is provided, a bendable part 325 that is provided adjacent to an operating part side of the distal end part 323 and is bendable, and a soft portion 326 that connects the bendable part 325 to the operating part 322. A closing operation of closing the grip part 324 and a bending operation of bending the bendable part 325 are input into the operating part 322. The treatment tool for an endoscope 320 further comprises a transmitting part 327 that transmits the operations of the operating part 322 to the grip part 324 and the bendable part 325.

The transmitting part 327 has a first transmitting member 328 that extends from the grip part 324 toward the operating part 322 and a second transmitting member 329 that extends from the bendable part 325 toward the operating part 322. The first transmitting member 328 and the second transmitting member 329 are accommodated inside the soft portion 326. The closing operation input into the operating part 322 is transmitted to the grip part 324 via the first transmitting member 328, and the bending operation input into the operating part 322 is transmitted to the bendable part 325 via the second transmitting member 329.

Figure 30:
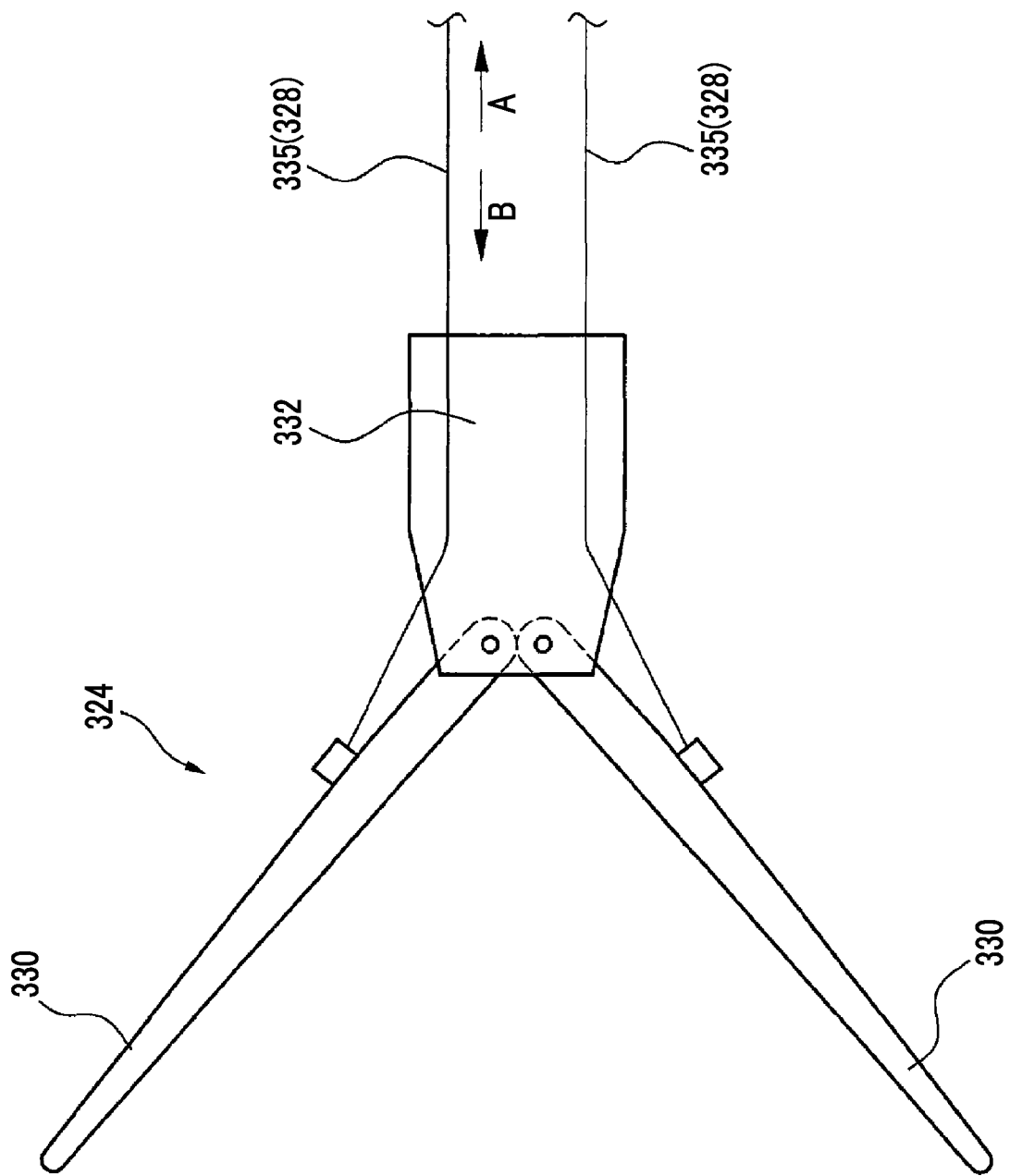
FIG. 30 is a view showing a grip part of the treatment tool for an endoscope of FIG. 29.
Figure 31:
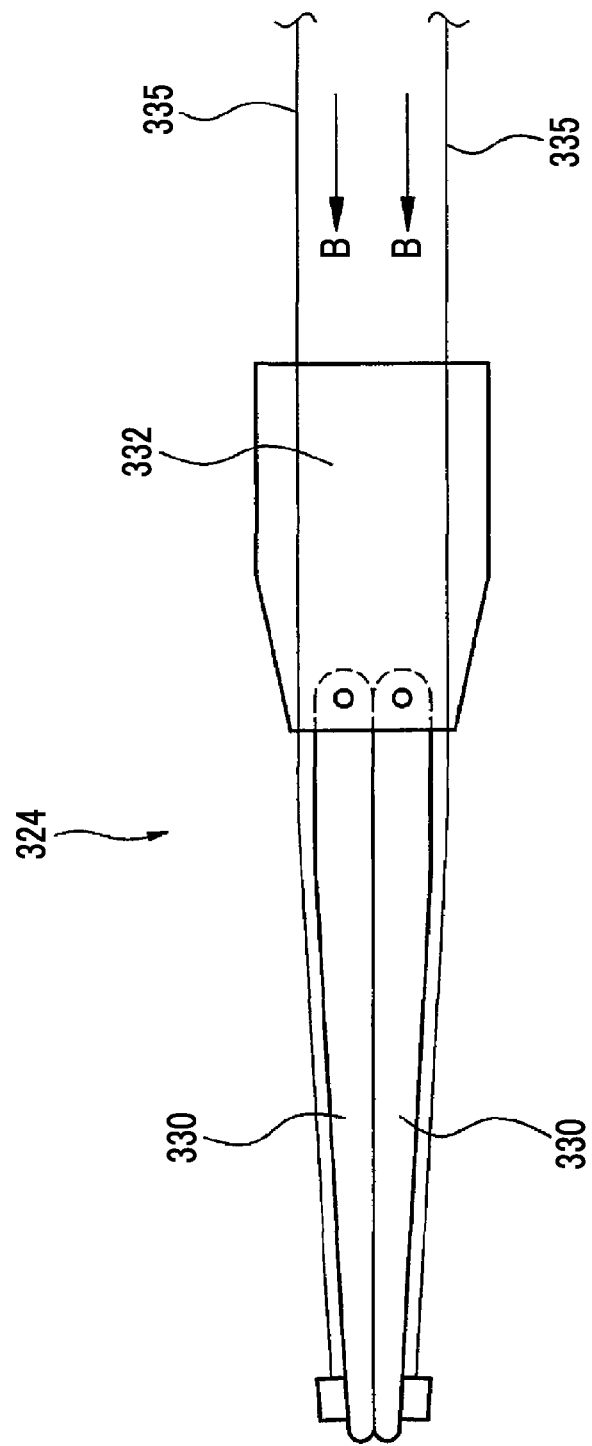
FIG. 31 is a view showing an operation of the grip part of FIG. 30.

FIGS. 30 and 31 show the grip part 324.

The grip part 324 has a pair of grip claws 330 and a support 332 that supports each of a proximal end part of the pair of grip claws 330 so as to be movable rotationally. As the first transmitting member 328 that transmits a closing operation of the operating part 322 to the grip part 324, two wires 335 are used, and the wires 335 are connected to the grip claws 330 so as to be movable in a longitudinal direction of the grip claws 330. Instead of the two wires 335, a single wire of which a distal end side is branched into two may be used.

The wire 335 is pushed out to a distal end part 323 side based on a closing operation of the operating part 322. Herein, as for a movement of the wire 335, pulling to an operating part 322 side is defined as a movement in the A-direction, and pushing out to the distal end part 323 side is defined as a movement in the B-direction. FIG. 30 shows a state where the wire 335 is pulled to the operating part 322 side, and distal end parts of the pair of grip claws 330 are open. By moving the wire 335 in the B-direction (first direction) based on a closing operation of the operating part 322, the distal end parts of the pair of grip claws 330 are closed as shown in FIG. 31.

Figure 32:
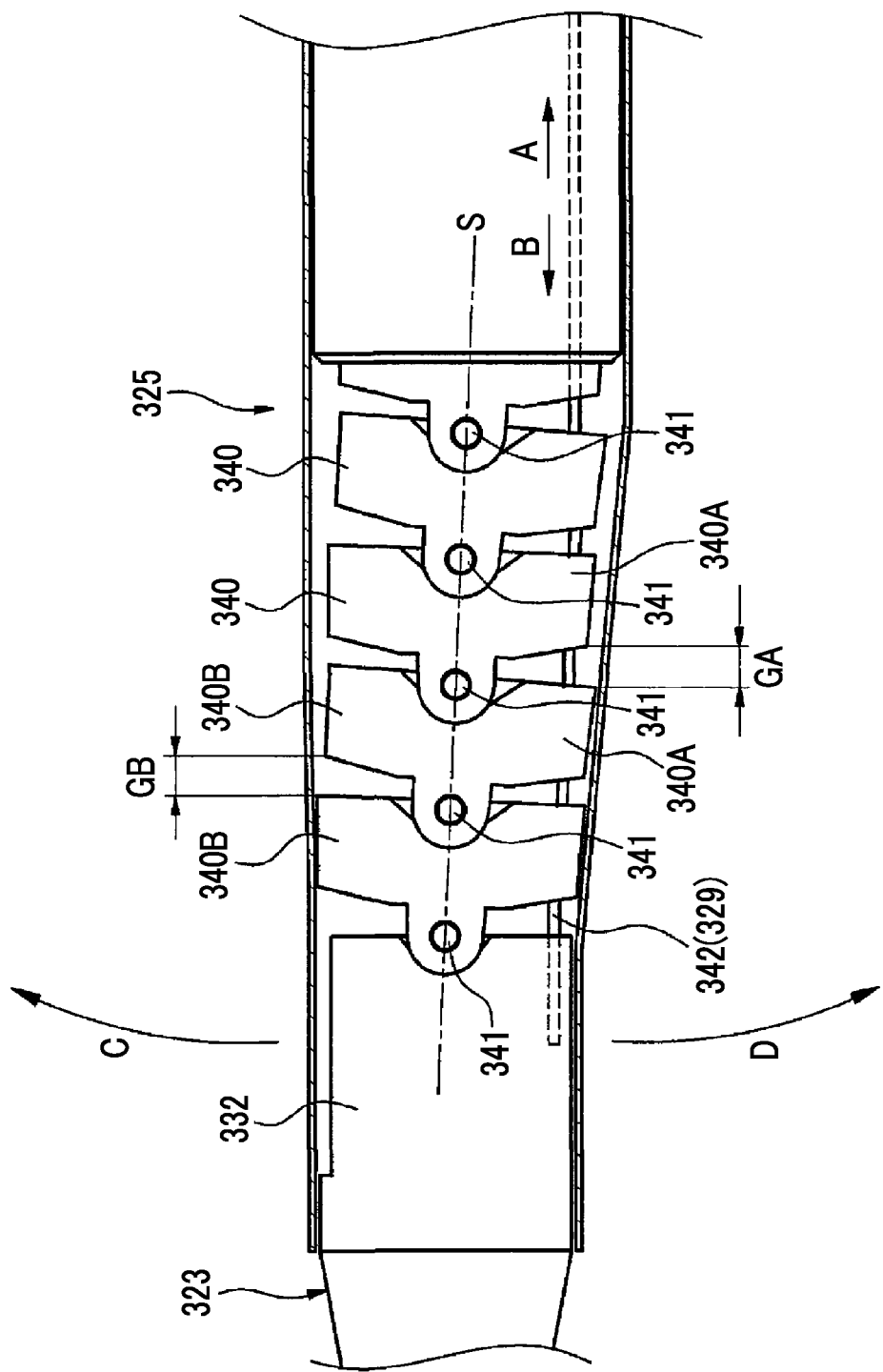
FIG. 32 is a view showing a bendable part of the treatment tool for an endoscope of FIG. 29.
Figure 33:
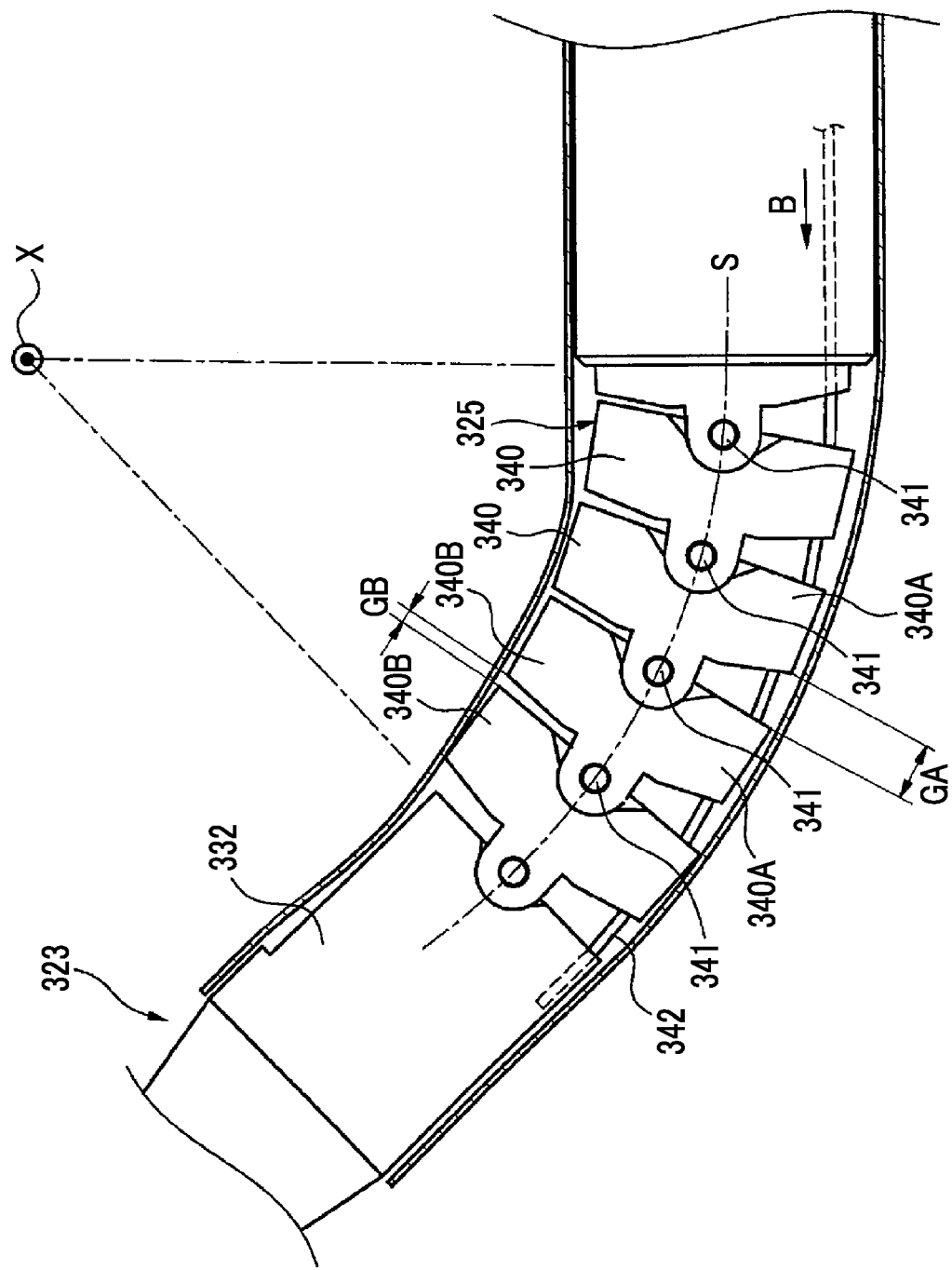
FIG. 33 is a view showing an operation of the bendable part of FIG. 32.

FIGS. 32 and 33 show the bendable part 325.

The bendable part 325 has a plurality of cyclic members 340 arranged in an axial direction of the insertion part 321, and two cyclic members 340 adjacent to each other are connected by a pair of pins 341 so as to be movable rotationally. The bending of the bendable part 325 is the sum of rotational movements of the plurality of cyclic members 340, and the bent neutral plane S of the bendable part 325 passes through the plurality of pins 341 arranged in the axial direction of the insertion part 321. In a case where the cyclic member 340 is divided into a first portion 340A and a second portion 340B with the bent neutral plane S as a boundary, there is the gap GA between the first portions 340A of the two cyclic members 340 adjacent to each other, and there is the gap GB also between the second portions 340B. Therefore, the bendable part 325 is bendable in the C-direction in which the gap GB on a second portion 340B side is narrowed, and is bendable also in the D-direction in which the gap GA on a first portion 340A side is narrowed.

The bendable part 325 is bendable in both directions including the C-direction and the D-direction, but is bent in the C-direction based on an operation of the operating part 322. As the second transmitting member 329 that transmits the operation of the operating part 322 to the bendable part 325, a wire 342 is used in the present example, and a distal end part of the wire 342 is connected to the support 332 of the distal end part 323. The wire 342 is pushed out to the distal end part 323 side based on the operation of the operating part 322. Herein, as for a movement of the wire 342, pulling to the operating part 322 side is defined as a movement in the A-direction, and pushing out to the distal end part 323 side is defined as a movement in the B-direction.

In the bending of the bendable part 325 in the C-direction, the first portion 340A of the cyclic member 340 is positioned on the bent outer diameter side, and the second portion 340B is positioned on the bent inner diameter side. As the wire 342 is disposed on the bent outer diameter side in the bending of the bendable part 325 in the C-direction and the wire 342 is moved in the B-direction (first direction) based on the bending operation of the operating part 322, the gap GA on the first portion 340A side between the two cyclic members 340 adjacent to each other is widened, conversely the gap GB on the second portion 340B side is narrowed, and the bendable part 325 is bent in the C-direction.

Figure 34:
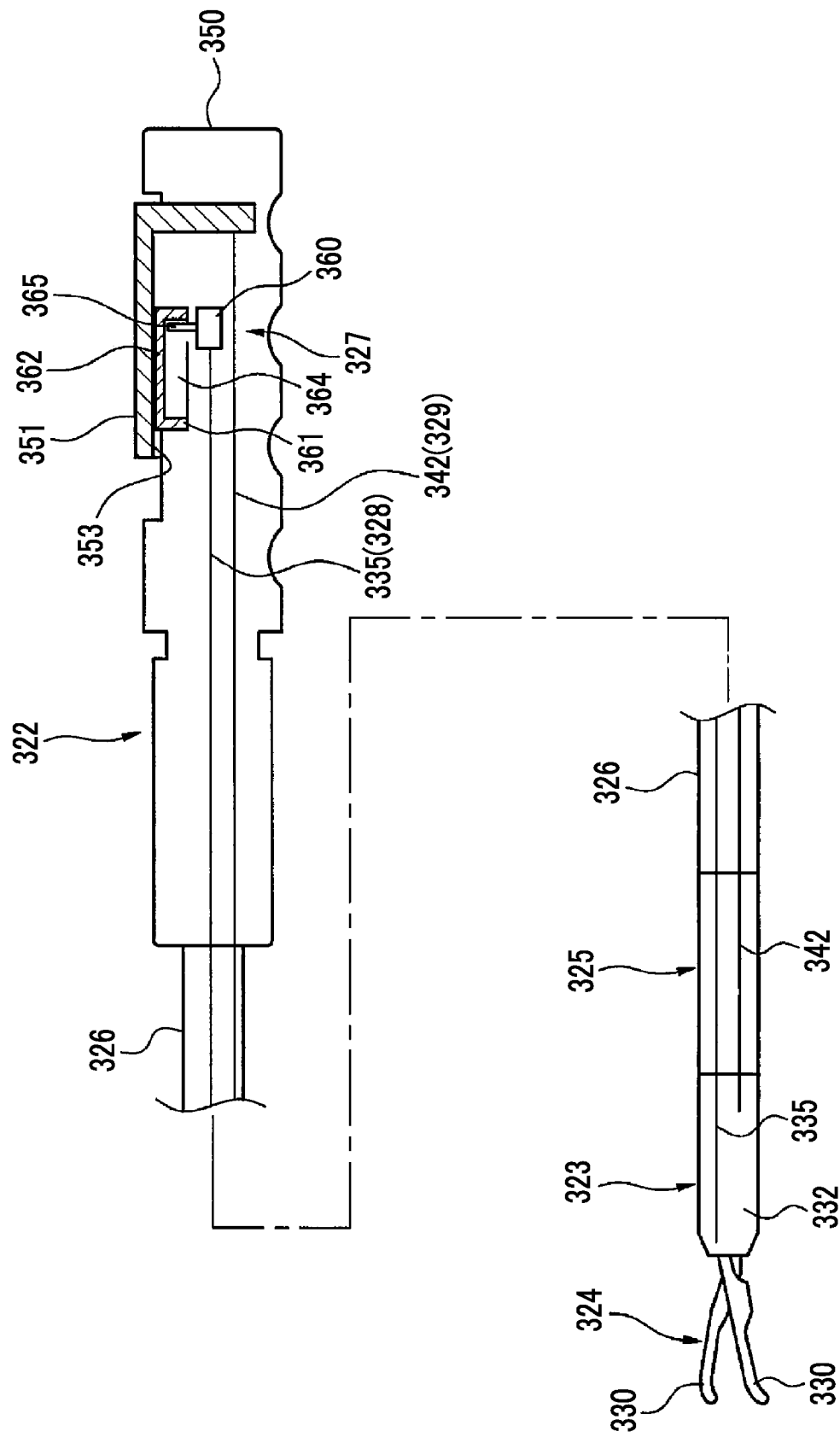
FIG. 34 is a view showing an operating part and a transmitting part of the treatment tool for an endoscope of FIG. 29.
Figure 35:
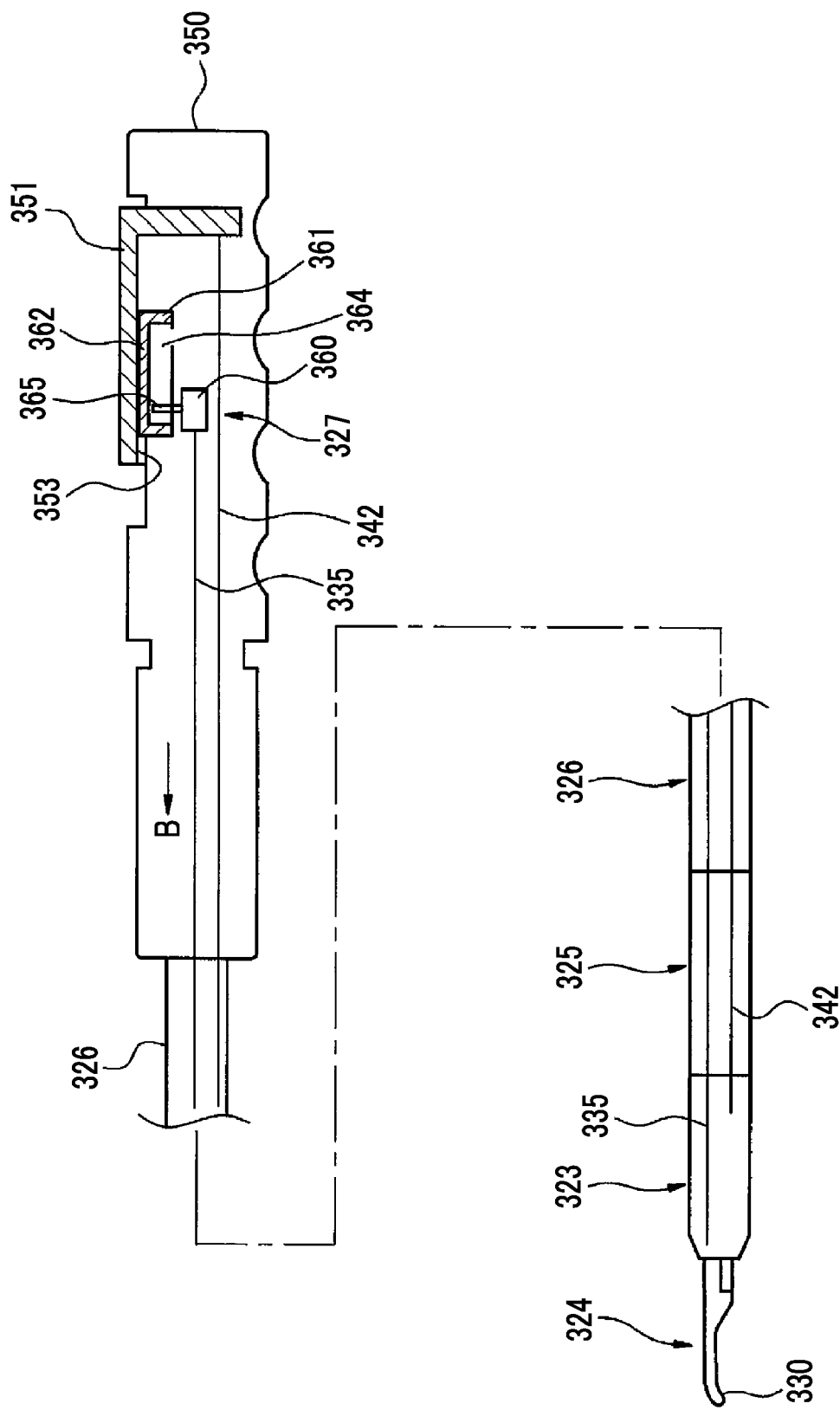
FIG. 35 is a view showing an operation of the transmitting part of the treatment tool for an endoscope of FIG. 29.
Figure 36:
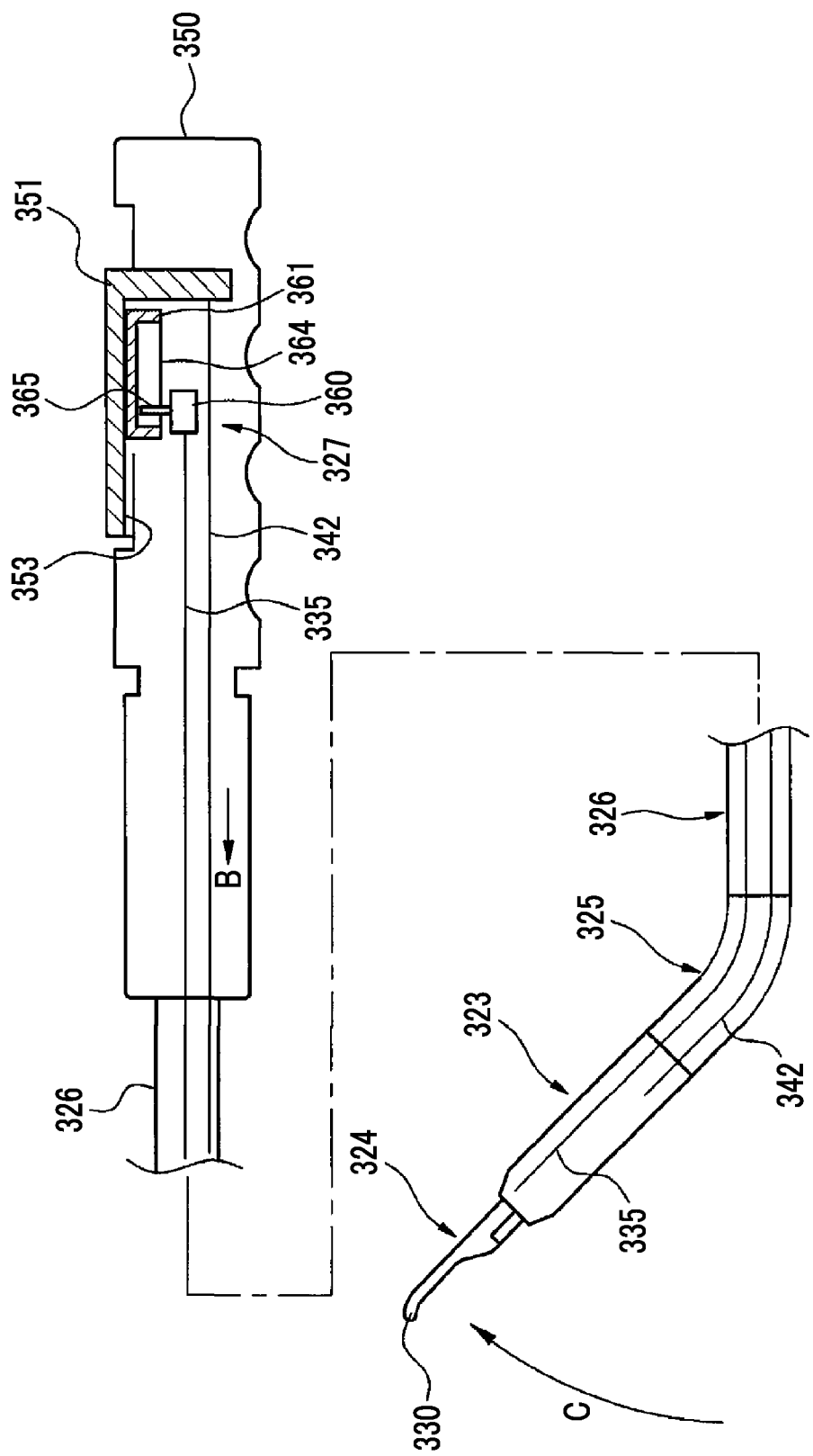
FIG. 36 is a view showing the operation of the transmitting part of the treatment tool for an endoscope of FIG. 29.

FIGS. 34 to 36 show the operating part 322 and the transmitting part 327.

The operating part 322 has an operating part body 350 and an operating member 351. The operating part body 350 is formed in a cylindrical shape, and the soft portion 326 is connected to a distal end part of the operating part body 350 on one side in the axial direction. The wire 335 which is the first transmitting member 328 and the wire 342 which is the second transmitting member 329 are drawn inside the operating part body 350. A central axis of the operating part body 350 is disposed on an extension of a central axis of the insertion part 321 or is disposed parallel to the central axis of the insertion part 321, and extends in the B-direction (first direction), which is a moving direction of the wire 335 and the wire 342. The operating member 351 is disposed on an outer peripheral surface of the operating part body 350 so as to be movable in the B-direction and is movable in the E-direction (second direction) orthogonal to the B-direction. Similar to the operating member 51 of the operating part 22 shown in FIG. 9, the E-direction may be a linear direction in a plane including the B-direction, or similar to the operating member 71 of the operating part 22 shown in FIG. 17, the E-direction may be a circumferential direction in the outer peripheral surface of the operating part body 350.

The transmitting part 327 has a follower member 360 and a cam member 361. The follower member 360 and the cam member 361 are provided inside the operating part body 350. The follower member 360 is movable only in the axial direction of the operating part body 350, that is, the B-direction. On the other hand, the cam member 361 is movable only in the E-direction perpendicular to the B-direction.

The cam member 361 has an engaging part 362, and the engaging part 362 extends in the B-direction. The operating member 351 is provided with an engaging part 353 that engages with the engaging part 362, and the engaging part 353 also extends in the B-direction. The engaging part 362 is formed in a convex shape in a cross section perpendicular to the B-direction, the engaging part 353 is formed in a concave shape in a cross section perpendicular to the B-direction, and a convex part of the engaging part 362 and a concave part of the engaging part 353 are fitted to each other. A side surface of the convex part of the engaging part 362 and a side surface of the concave part of the engaging part 353 extend in the B-direction and intersect the E-direction. The engaging part 362 may be formed in a concave shape, and the engaging part 353 may be formed in a convex shape.

Based on the engagement between the side surface of the engaging part 353 and the side surface of the engaging part 362, a relative movement in the B-direction between the operating member 351 and the cam member 361 is allowed, and a relative movement in the E-direction is prevented. The movement of the operating member 351 in the B-direction is not transmitted to the cam member 361, and the operating member 351 is independently moved in the B-direction. On the other hand, the movement of the operating member 351 in the E-direction is transmitted to the cam member 361, and the cam member 361 and the operating member 351 are moved in the E-direction integrally with each other.

In addition, the cam member 361 has a cam groove 364, and the follower member 360 has a cam pin 365. The cam pin 365 engages with the cam groove 364 so as to be movable in an extending direction of the cam groove 364. The cam groove 364 extends in the third direction intersecting the B-direction and the E-direction, in a plane where the cam member 361 moves. In a case where the cam member 361 is moved in the E-direction, the cam pin 365 is moved in the cam groove 364 in the third direction, and the follower member 360 is moved in the B-direction in response to the movement of the cam pin 365.

The wire 335, which is the first transmitting member 328, is connected to the follower member 360, and the wire 342, which is the second transmitting member 329, is connected to the operating member 351. As described above, the cam member 361 is moved in the E-direction in response to an operation of the operating member 351 in the E-direction, and the follower member 360 is moved in the B-direction based on the movement of the cam member 361 in the E-direction. Accordingly, the wire 335 is moved in the B-direction, and the grip part 324 is closed. In a case where the grip part 324 is closed, the operating member 351 is operated in the E-direction, and is not moved in the B-direction orthogonal thereto. The wire 342 connected to the operating member 351 is also not moved in the B-direction, and the bendable part 325 is maintained in a linear shape.

Next, in response to an operation of the operating member 351 in the B-direction, the wire 342 is moved in the B-direction, and the bendable part 325 is bent as described above. In a case where the bendable part 325 is bent, the operating member 351 is operated in the B-direction, and is not moved in the E-direction orthogonal thereto. Therefore, the follower member 360 is not moved in the B-direction via the cam member 361, and the grip part 324 is maintained in a closed state.

The wire 335 for closing the grip part 324 may be connected to the operating member 351, and the wire 342 for bending the bendable part 325 may be connected to the follower member 360. In this case, the grip part 324 is closed as the operating member 351 is operated in the B-direction, and the bendable part 325 is bent as the operating member 351 is operated in the E-direction.

The treatment tool for an endoscope 320 is used, for example, in the treatment method shown in FIGS. 18 to 21. First, the grip part 324 is closed based on an operation of the operating part 322, and the lesion part LA is gripped by the grip part 324. Then, after the lesion part LA is gripped by the grip part 324, the bendable part 325 is bent based on the operation of the operating part 322. Accordingly, the grip part 324 is erected, and the lesion part LA gripped by the grip part 324 is lifted.

In the treatment method described above, the gripping of the lesion part LA by closing the grip part 324 and the lifting of the lesion part LA by bending the bendable part 325 are performed only with an operation of the operating member 351 of the operating part 322 as described above. A closing operation of closing the grip part 324 and a bending operation of bending the bendable part 325 are independent of each other, and in a case where the grip part 324 is closed, the bendable part 325 is maintained in a linear shape, and a relative movement between the grip part 324 and the lesion part LA is prevented. Accordingly, the gripping of the lesion part LA and the lifting of the gripped lesion part LA can be easily performed with an operation of the treatment tool for an endoscope 320 alone.

Just as the wire 342 for bending the bendable part 325, the wire 335 for closing the grip part may be disposed on the bent outer diameter side in the bending of the bendable part 325 in the C-direction, or may be disposed on the bent inner diameter side or the bent neutral plane S. In a case where the wire 335 is disposed on the bent inner diameter side, the grip part 324 is pressed against the lesion part LA as the bendable part 325 is bent in the D-direction opposite to the C-direction even though the bendable part 325 is bent due to the friction of the wire 335. In addition, in a case where the wire 335 is disposed on the bent neutral plane S, the bending of the bendable part 325 caused by the friction of the wire 335 is further prevented. Accordingly, a relative movement between the grip part 324 and the lesion part LA gripped by the grip part 324 is prevented, and the gripping of the lesion part LA becomes easier.

Further, the bendable part 325 may be configured to be not bendable in the D-direction. In this case, the bending of the bendable part 325 caused by the friction of the wire 335 is reliably prevented.

Figure 37:
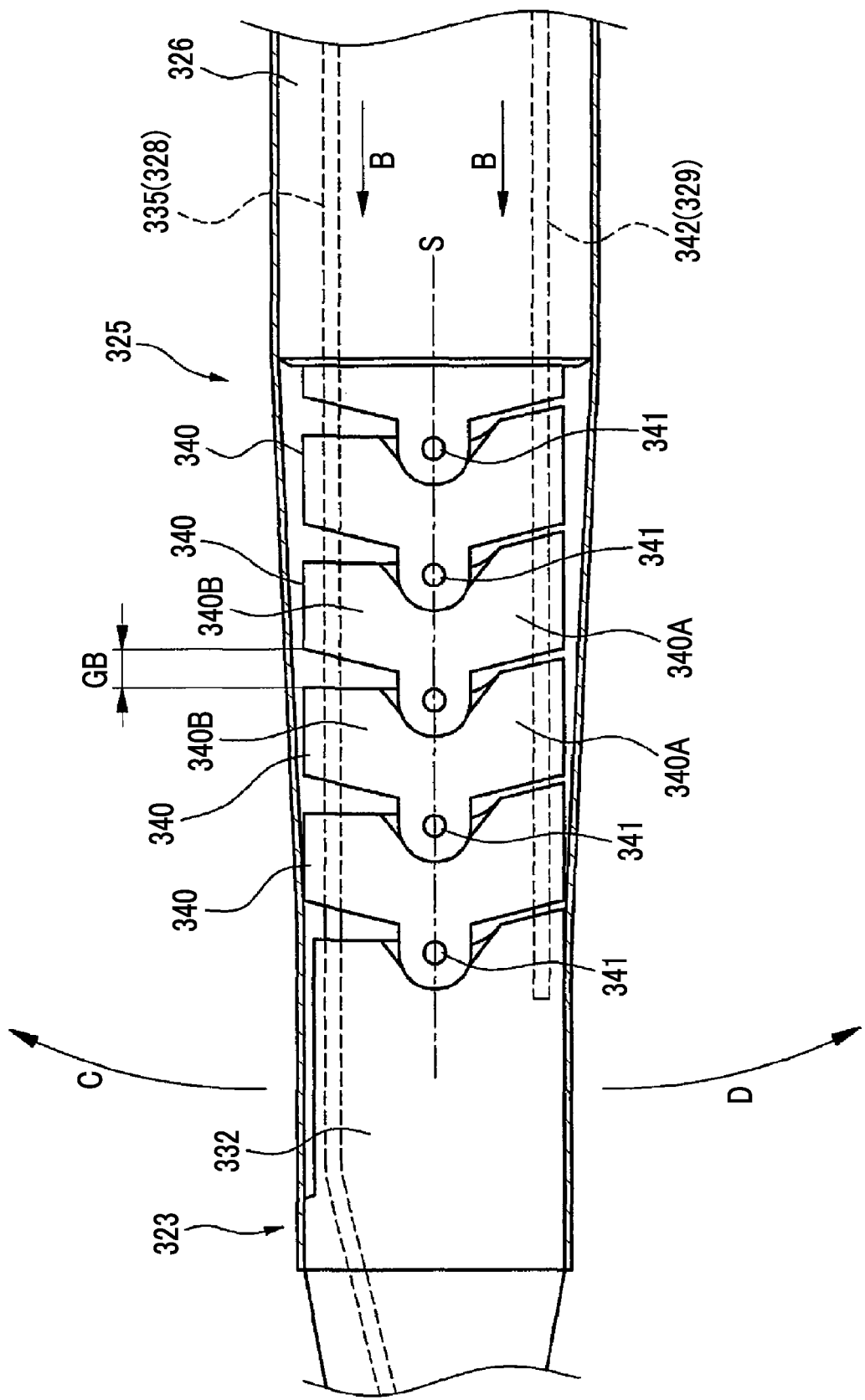
FIG. 37 is a view showing a modification example of the bendable part of FIG. 32.
Figure 38:
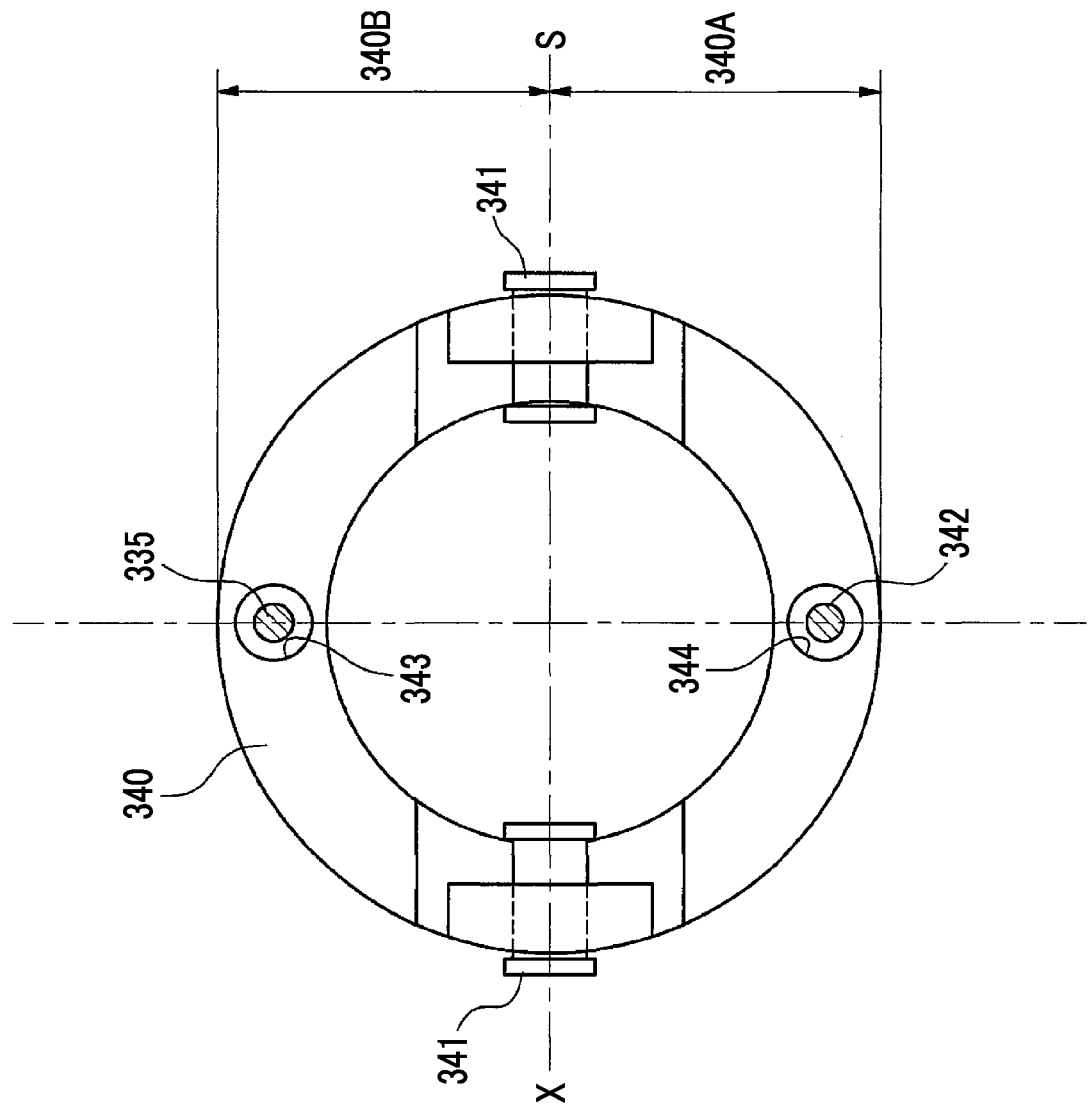
FIG. 38 is a view showing a cross section of the bendable part of FIG. 37.

In a case where the cyclic member 340 is divided into the first portion 340A and the second portion 340B with the bent neutral plane S of the bendable part 325 as a boundary, the second portions 340B of the two cyclic members 340 adjacent to each other are contactless with the gap GB therebetween, in the bendable part 325 shown in FIGS. 37 and 38, but the first portions 340A are in contact with each other. Therefore, the bendable part 325 is bendable only in the C-direction, in which the gap GB is narrowed, and is not bendable in the D-direction opposite to the C-direction.

In the bending of the bendable part 325 in the C-direction, the first portion 340A of the cyclic member 340 is positioned on the bent outer diameter side, and the second portion 340B is positioned on the bent inner diameter side. A first guide 343 that holds the wire 335 which is the first transmitting member 328 is provided at the second portion 340B, and the wire 335 is disposed on the bent outer diameter side. A second guide 344 that holds the wire 342 which is the second transmitting member 329 is provided at the first portion 340A, and the wire 342 is disposed on the bent inner diameter side.

The gap GB is narrowed as the wire 342 is moved in the B-direction, and thus the bendable part 325 is bent in the C-direction. In a case where the wire 335 is disposed on the bent outer diameter side which is an opposite side to the wire 342 with the bent neutral plane S interposed therebetween and the bendable part 325 is bent due to the friction of the wire 335 moved in the B-direction, the bendable part 325 is bent in the D-direction opposite to the C-direction, but the bendable part 325 is not bendable in the D-direction. Therefore, based on an operation of the operating part 322, the wire 335 is moved in the B-direction, and in a case where the grip part 324 is closed, the bendable part 325 is reliably maintained in a linear shape. Accordingly, a relative movement between the grip part 324 and the lesion part LA gripped by the grip part 324 is prevented, and the gripping of the lesion part LA becomes even easier.

The wire 335 may be disposed on the bent neutral plane S. In a case where the wire 335 is disposed on the bent neutral plane S, the first guide 343 holding the wire 335 is provided, for example, at an end part of the pin 341.

Figure 39:
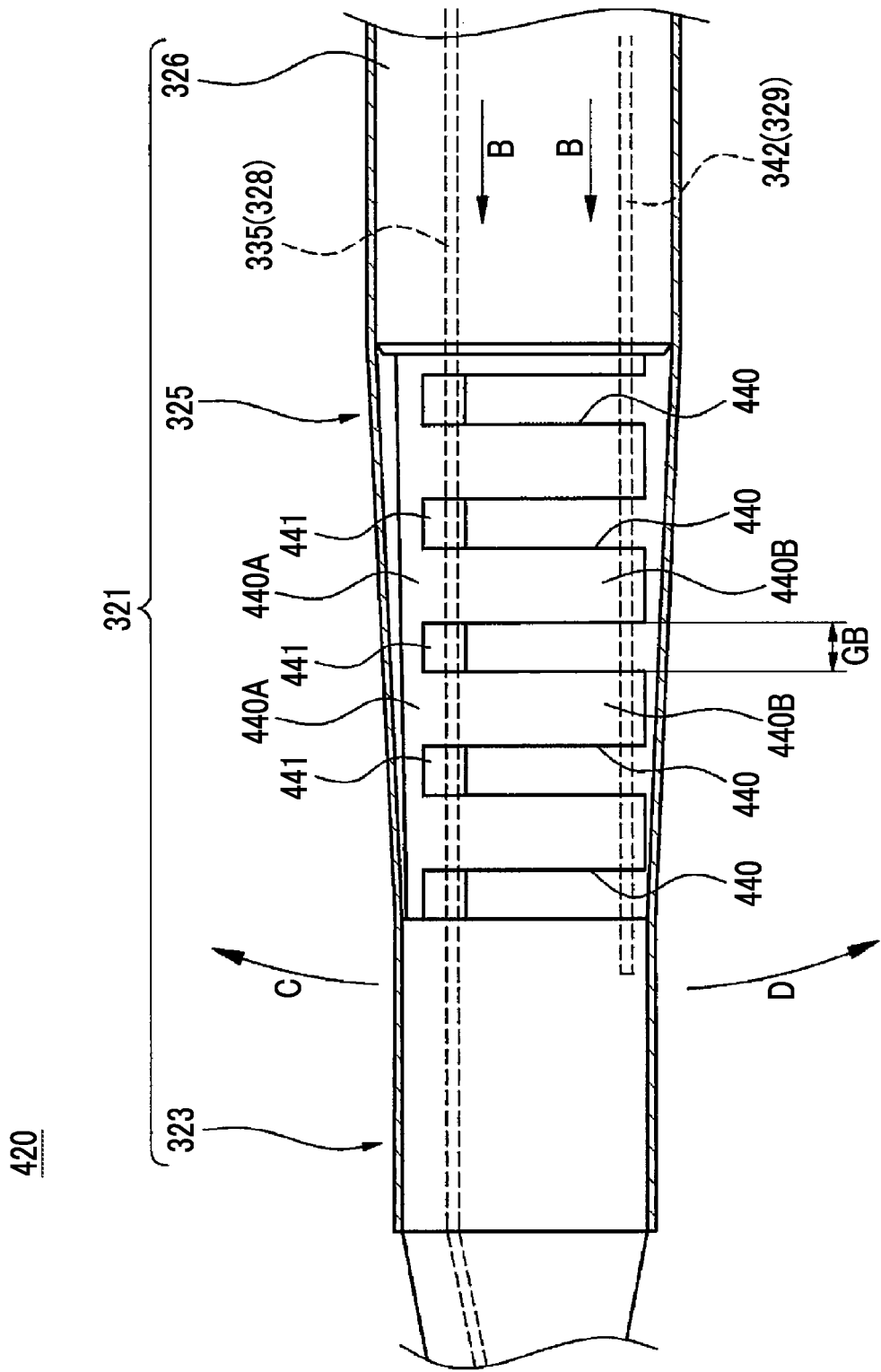
FIG. 39 is a view showing still another example of the bendable part of the treatment tool for an endoscope, which is for describing Embodiment 1 of the present invention.
Figure 40:
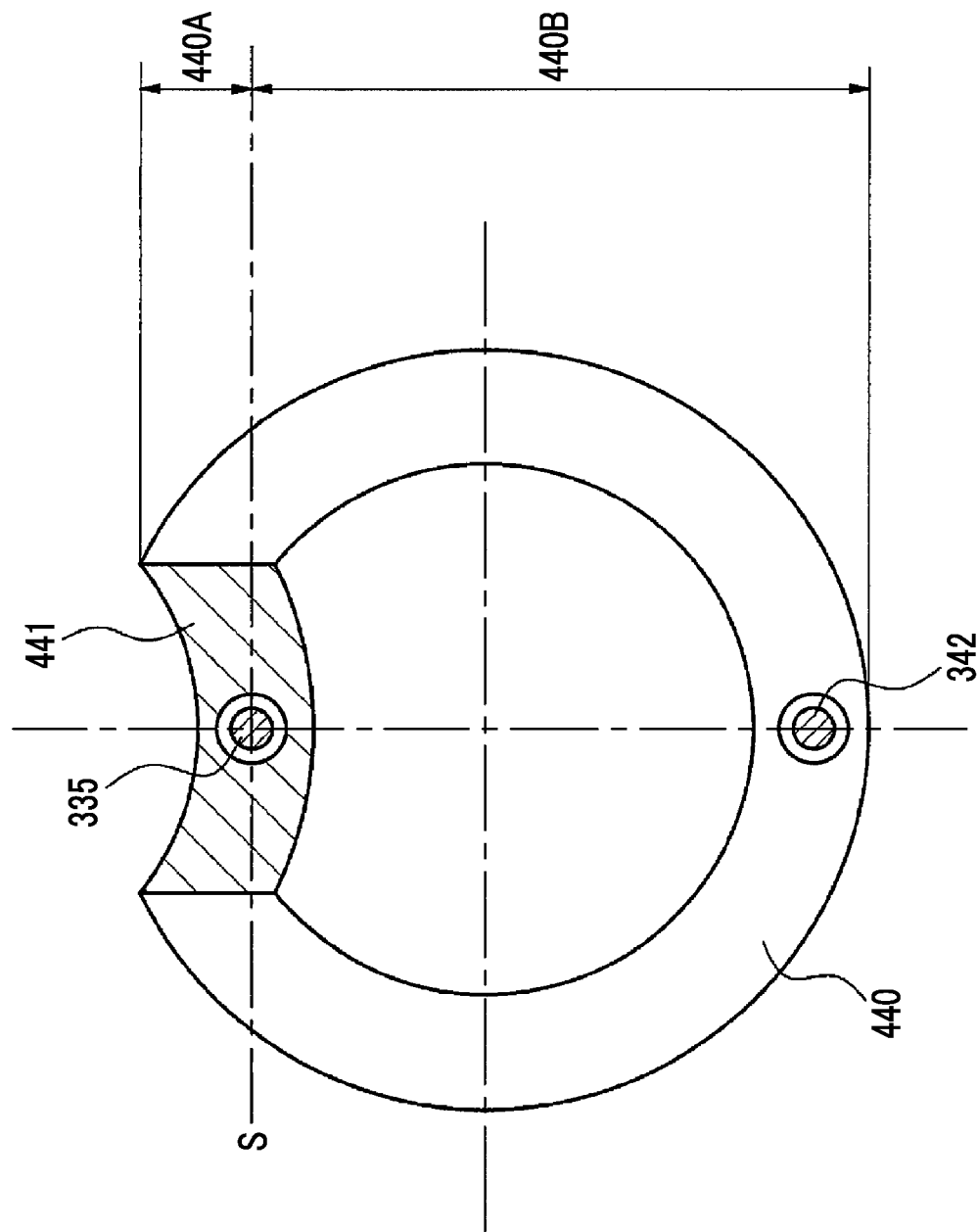
FIG. 40 is a view showing a cross section of the bendable part of FIG. 39.

Also a treatment tool for an endoscope 420 shown in FIGS. 39 and 40 is also configured such that the bendable part is bendable in one direction and is not bendable in an opposite direction. The treatment tool for an endoscope 420 and the treatment tool for an endoscope 320 described above are different from each other only in terms of the configuration of the bendable part. Thus, common elements will be assigned with common reference numerals, and description thereof will be omitted.

An insertion part 421 of the treatment tool for an endoscope 420 comprises the distal end part 323, a bendable part 425, and the soft portion 326. The bendable part 425 has a plurality of cyclic portions 440 arranged in an axial direction of the insertion part 421 and one or more connecting portions 441 that connect two cyclic portions 440 adjacent to each other. The cyclic portions 440 and the connecting portions 441 are formed integrally with each other. In a cross section perpendicular to the axial direction of the insertion part 421, the connecting portions 441 are formed in an arc shape that is convex to a central axis side of the insertion part 421.

In a case where the cyclic portion 440 is divided into a first portion 440A connected to the connecting portion 441 and a second portion 440B excluding the first portion 440A, there is the gap GB between the second portions 440B of the two cyclic portions 440 adjacent to each other. The connecting portion 441 having an arc-shaped cross section is capable of only bending a concave surface inward of bending the concave surface inward or bending the concave surface outward. Therefore, the bendable part 425 is bendable only in the C-direction, in which the gap GB is widened, with the bending of the concave surface of the connecting portion 441 inward, and is not bendable in the D-direction opposite to the C-direction. The bent neutral plane S of the bendable part 425 passes through a circumferential middle portion of each of the plurality of connecting portions 441 arranged in the axial direction of the insertion part 421.

The wire 342 which is the second transmitting member 329 is disposed on the bent outer diameter side in the bending of the bendable part 425 in the C-direction. The gap GB is widened as the wire 342 is moved in the B-direction, and thus the bendable part 425 is bent in the C-direction. The wire 335 which is the first transmitting member 328 is disposed on the bent neutral plane S of the bendable part 425. Since the bendable part 425 is not bendable in the D-direction opposite to the C-direction, based on an operation of the operating part 322, the wire 335 is moved in the B-direction, and in a case where the grip part 324 is closed, the bendable part 425 is reliably maintained in a linear shape. Accordingly, a relative movement between the grip part 324 and the lesion part LA gripped by the grip part 324 is prevented, and the gripping of the lesion part LA becomes even easier.

Embodiment 2

Although the transmitting parts 27 and 327 and the operating parts 22 and 322 having the follower member and the cam member have been described in Embodiment 1, the configurations of the transmitting part and the operating part are not limited thereto. A modification example of the transmitting part and the operating part will be described in Embodiment 2, and portions which are the same as in Embodiment 1 will be not be described.

Figure 41:
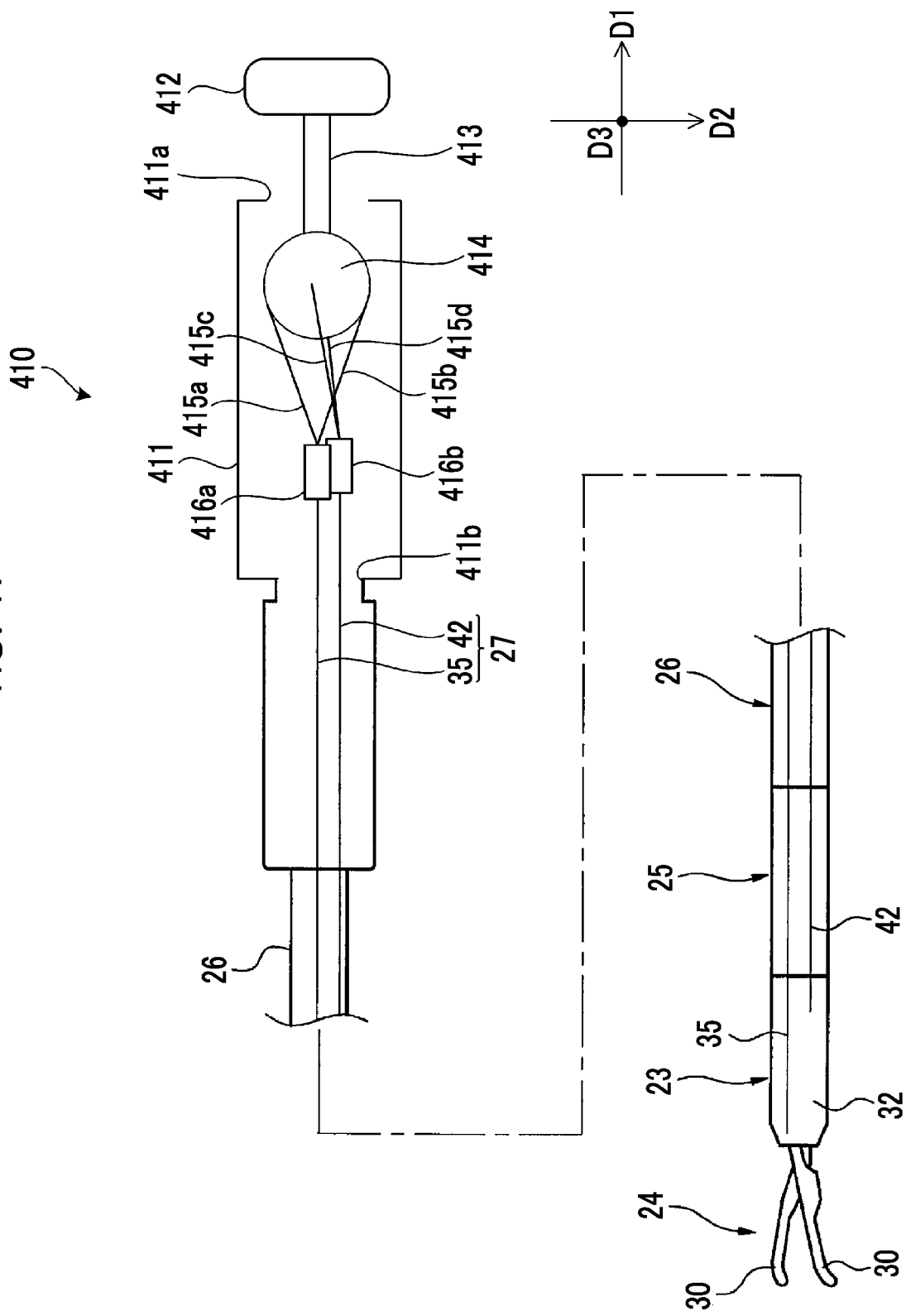
FIG. 41 is a view showing Modification Example 1 of the transmitting part and the operating part of the treatment tool for an endoscope, which is for describing Embodiment 2 of the present invention.

FIG. 41 is a view showing Modification Example 1 of the transmitting part and the operating part of the treatment tool for an endoscope, which is for describing Embodiment 2 of the present invention. In FIG. 41, portions which are the same as the portions shown in FIG. 10 will be assigned with the same reference numerals, and description thereof will be omitted. As shown in FIG. 41, a joystick-type operating part 410 may be provided instead of the operating part 22.

In an example of FIG. 41, the transmitting part 27 has the wire 35 which is the first transmitting member 28 and the wire 42 which is the second transmitting member 29. A direction parallel to the A-direction (a longitudinal axis of the insertion part 21) that is a pulling direction of the wires 35 and 42 will be defined as a D1-direction (first direction). A direction orthogonal to the D1-direction will be defined as a D2-direction (second direction). A direction orthogonal to the D1-direction and the D2-direction will be defined as a D3-direction (third direction).

The operating part 410 has a gripped part 411, a finger placing part 412, a support column part 413, a sphere 414, wires 415a to 415d, and connecting portions 416a and 416b.

The gripped part 411 is formed in a hollow cylindrical shape, and is gripped by, for example, the palm and four fingers excluding the thumb of one hand of a user. The gripped part 411 has an opening portion 411a in an upper surface thereof, and has an opening portion 411b in a lower surface c. The sphere 414, the wires 415a to 415d, and the connecting portions 416a and 416b are provided inside the hollow gripped part 411.

The finger placing part 412 and the support column part 413 are examples of a lever part that can be tilted with respect to the gripped part 411 with an operation by the thumb of the hand of the user gripping the gripped part 411. The finger placing part 412 is a portion where the thumb of the user gripping the gripped part 411 is placed, and is formed in a chamfered cylindrical shape.

The support column part 413 is a member that is formed in a cylindrical shape and connects the finger placing part 412 outside the gripped part 411 to the sphere 414 inside the gripped part 411. The support column part 413 is movable in the opening portion 411a of the gripped part 411. In a state where the gripped part 411 is not operated, an axial direction of the support column part 413 and an axial direction of the gripped part 411 match each other as shown in FIG. 41.

The sphere 414 is an example of a rotational movement body that is provided so as to be movable rotationally inside the gripped part 411 and is connected to the finger placing part 412 and the support column part 413. The finger placing part 412 and the support column part 413 are movable rotationally about the sphere 414. As the user gripping the operating part 410 operates the finger placing part 412 with the thumb, the finger placing part 412 and the support column part 413 can be tilted with respect to the gripped part 411.

The wires 415a to 415d are four wires having the same length, and are provided so as to be movable inside the gripped part 411. A first end of each of the wires 415a and 415b is fixed to the connecting portion 416a. The wires 415a and 415b are examples of a first wire. A first end of each of the wires 415c and 415d is fixed to the connecting portion 416b. The wires 415c and 415d are examples of a second wire.

A second end of each of the wires 415a to 415d is fixed at four places on the surface of the sphere 414. The four places are four places at equal intervals on an outer periphery of a cross section in a case where the sphere 414 is bisected by a plane orthogonal to the axial direction of the support column part 413. Specifically, the second ends of the wires 415a and 415b are fixed at two points respectively on the surface of the sphere 414, which intersect a straight line passing through the center of the sphere 414 in the D2-direction. The second ends of the wires 415c and 415d are fixed at two points respectively on the surface of the sphere 414, which intersect a straight line passing through the center of the sphere 414 in the D3-direction.

The connecting portion 416a is a member that connects one end of the wire 35 to the first end of each of the wires 415a and 415b, and is provided so as to be movable inside the gripped part 411. The wire 35 is connected from the connecting portion 416a to the distal end part 23 through the opening portion 411b of the gripped part 411.

The connecting portion 416b is a member that connects one end of the wire 42 to the first end of each of the wires 415c and 415d, and is provided so as to be movable inside the gripped part 411. The wire 42 is connected from the connecting portion 416b to the bendable part 25 through the opening portion 411b of the gripped part 411.

The wire 35 which is the first transmitting member 28 moves in the A-direction (D1-direction) according to the tilting of the finger placing part 412 and the support column part 413 (lever parts) in the D2-direction. The wire 42 which is the second transmitting member 29 moves in the A-direction (D1-direction) according to the tilting of the finger placing part 412 and the support column part 413 (lever parts) in the D3-direction. Then, the grip part 24 is closed as the wire 35 is moved in the A-direction. In addition, the bendable part 25 is bent as the wire 42 is moved in the A-direction.

FIG. 41 shows a state where the finger placing part 412 and the support column part 413 are not tilted with respect to the gripped part 411. In this state, the grip part 24 is open, and the bendable part 25 extends in a linear shape.

Figure 42:
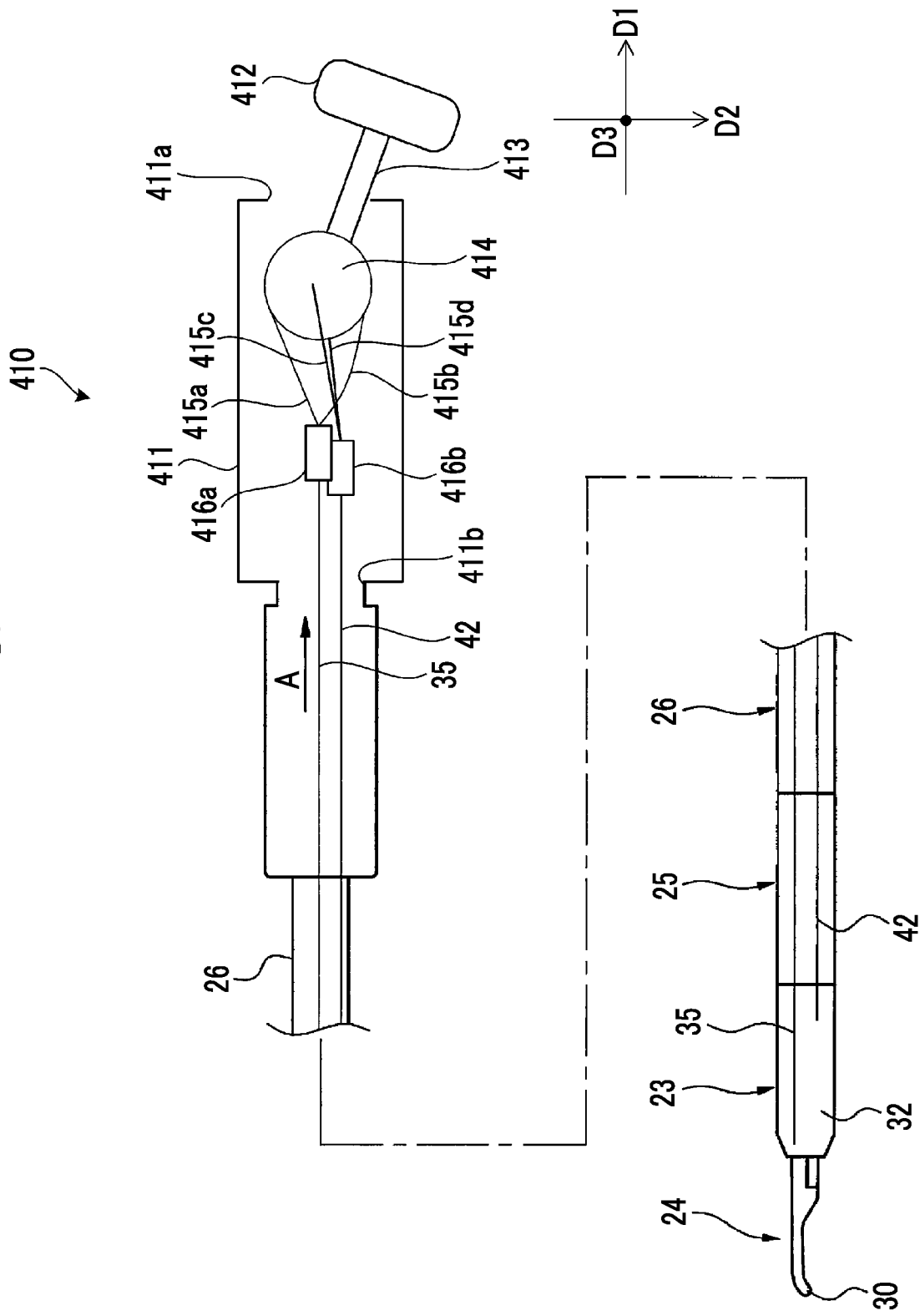
FIG. 42 is a view showing an operation of the transmitting part of FIG. 41.

In a case where an operation of tilting the finger placing part 412 and the support column part 413 with respect to the gripped part 411 in the D2-direction is performed in the state shown in FIG. 41, the sphere 414 is moved rotationally by a rotational movement shaft in the D3-direction. As shown in FIG. 42, due to the rotational movement of the sphere 414, the wire 415a is pulled to an opposite direction to the connecting portion 416a, and the connecting portion 416a moves in the A-direction. In this case, the wire 415b does not hinder the movement of the connecting portion 416a in the A-direction by bending.

In addition, since portions of the surface of the sphere 414, which are fixed to the wires 415c and 415d, do not move due to the rotational movement of the sphere 414, the wires 415c and 415d and the connecting portion 416b do not move. For this reason, in the state shown in FIG. 42, only the wire 35 connected to the connecting portion 416a, of the wires 35 and 42, is pulled in the A-direction. Therefore, the grip part 24 is closed, but the bendable part 25 remains being extended in a linear shape.

Figure 43:
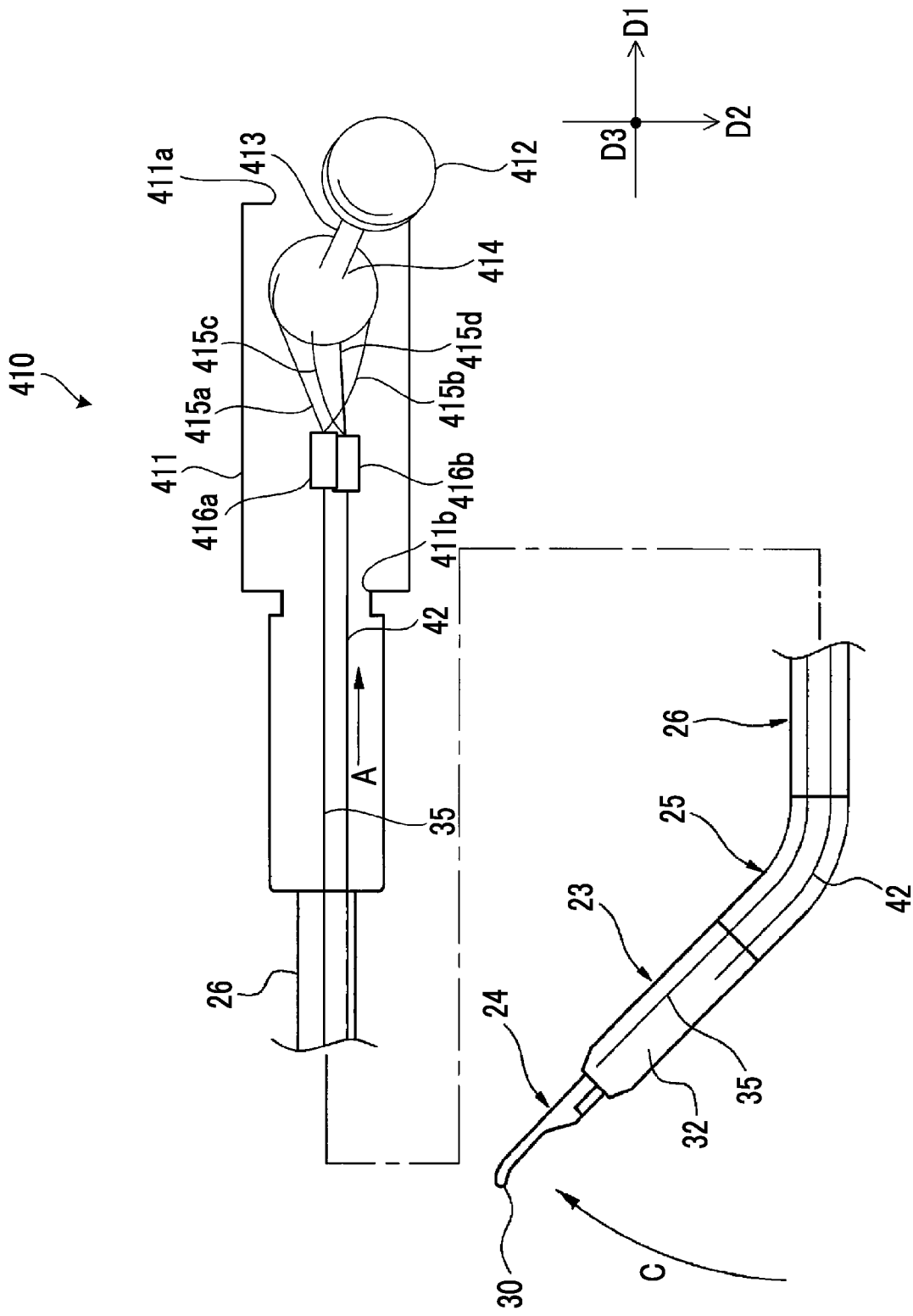
FIG. 43 is a view showing the operation of the transmitting part of FIG. 41.

In a case where an operation of tilting the finger placing part 412 and the support column part 413 with respect to the gripped part 411 further in the D3-direction is performed in the state shown in FIG. 42, the sphere 414 is moved rotationally by a rotational movement shaft in the D2-direction. As shown in FIG. 43, due to the rotational movement of the sphere 414, the wire 415d is pulled to an opposite direction to the connecting portion 416b, and the connecting portion 416b moves in the A-direction. In this case, the wire 415d does not hinder the movement of the connecting portion 416b in the A-direction by bending. Therefore, the bendable part 25 is bent while the grip part 24 is closed.

That is, in a state where the finger placing part 412 and the support column part 413 are not tilted with respect to the gripped part 411 as shown in FIG. 41, the grip part 24 is open, and the bendable part 25 extends in a linear shape. In a case where an operation of first tilting the finger placing part 412 and the support column part 413 with respect to the gripped part 411 in the D2-direction from this state and then tilting the finger placing part 412 and the support column part 413 with respect to the gripped part 411 in the D3-direction is performed, first, the grip part 24 is closed as shown in FIG. 42, and next the bendable part 25 is bent as shown in FIG. 43.

As described above, the operating part 410 of Modification Example 1 comprises the finger placing part 412 and the support column part 413 that can be tilted with respect to the gripped part 411 with an operation by the thumb of the hand of the user gripping the gripped part 411. Thus, the wire 35 moves in the D1-direction (A-direction) according to the tilting of the finger placing part 412 and the support column part 413 in the D2-direction, and the wire 42 moves in the D1-direction (A-direction) according to the tilting of the finger placing part 412 and the support column part 413 in the D3-direction. Then, the grip part 24 is closed as the wire 35 is moved in the A-direction, and the bendable part 25 is bent as the wire 42 is moved in the A-direction.

For this reason, the gripping of the lesion part and the lifting of the gripped lesion part can be performed with an operation that is easy to exert a force, such as tilting the finger placing part 412 and the support column part 413 (lever parts) with the thumb of the hand gripping the gripped part 411.

In addition, the gripping of the lesion part LA by closing the grip part 24 and the lifting of the lesion part LA by bending the bendable part 25 are performed only with an operation of the finger placing part 412. A closing operation of closing the grip part 24 and a bending operation of bending the bendable part 25 are independent of each other, and in a case where the grip part 24 is closed, the bendable part 25 is maintained in a linear shape, and a relative movement between the grip part 24 and the lesion part LA is prevented. Accordingly, the gripping of the lesion part LA and the lifting of the gripped lesion part LA can be easily performed with an operation of the treatment tool for an endoscope 20 alone.

In addition, the operating part 410 of Modification Example 1 has the sphere 414 (rotational movement body) that is movable rotationally inside the gripped part 411 and is connected to the finger placing part 412 and the support column part 413 (lever parts), the wires 415a and 415b (first wires) that are fixed to the sphere 414 and are connected to the wire 35, and the wires 415c and 415d (second wires) that are fixed to the portions of the sphere 414, which are different from the portions to which the wires 415a and 415b are fixed, and are connected to the wire 42.

The wire 35 is pulled by the wires 415a and 415b in response to a rotational movement of the sphere 414 caused by the tilting of the finger placing part 412 and the support column part 413 in the D2-direction and moves in the D1-direction (A-direction). The wire 42 is pulled by the wires 415c and 415d in response to a rotational movement of the sphere 414 caused by the tilting of the finger placing part 412 and the support column part 413 in the D3-direction and moves in the D1-direction (A-direction).

The wires 415a and 415b are two wires fixed to two portions of the surface of the sphere 414, which intersect a straight line passing through a rotational movement center of the sphere 414 in the D2-direction. By providing the wires 415a and 415b, the grip part 24 can be closed by pulling the wire 35 even though the finger placing part 412 and the support column part 413 are tilted to any side in the D2-direction. However, a configuration where one of the wires 415a and 415b is omitted may be adopted.

The wires 415c and 415d are two wires fixed to two portions of the surface of the sphere 414, which intersect a straight line passing through the rotational movement center of the sphere 414 in the D3-direction. By providing the wires 415c and 415d, the bendable part 25 can be bent by pulling the wire 42 even though the finger placing part 412 and the support column part 413 are tilted to any side in the D3-direction. However, a configuration where one of the wires 415c and 415d is omitted may be adopted.

Figure 44:
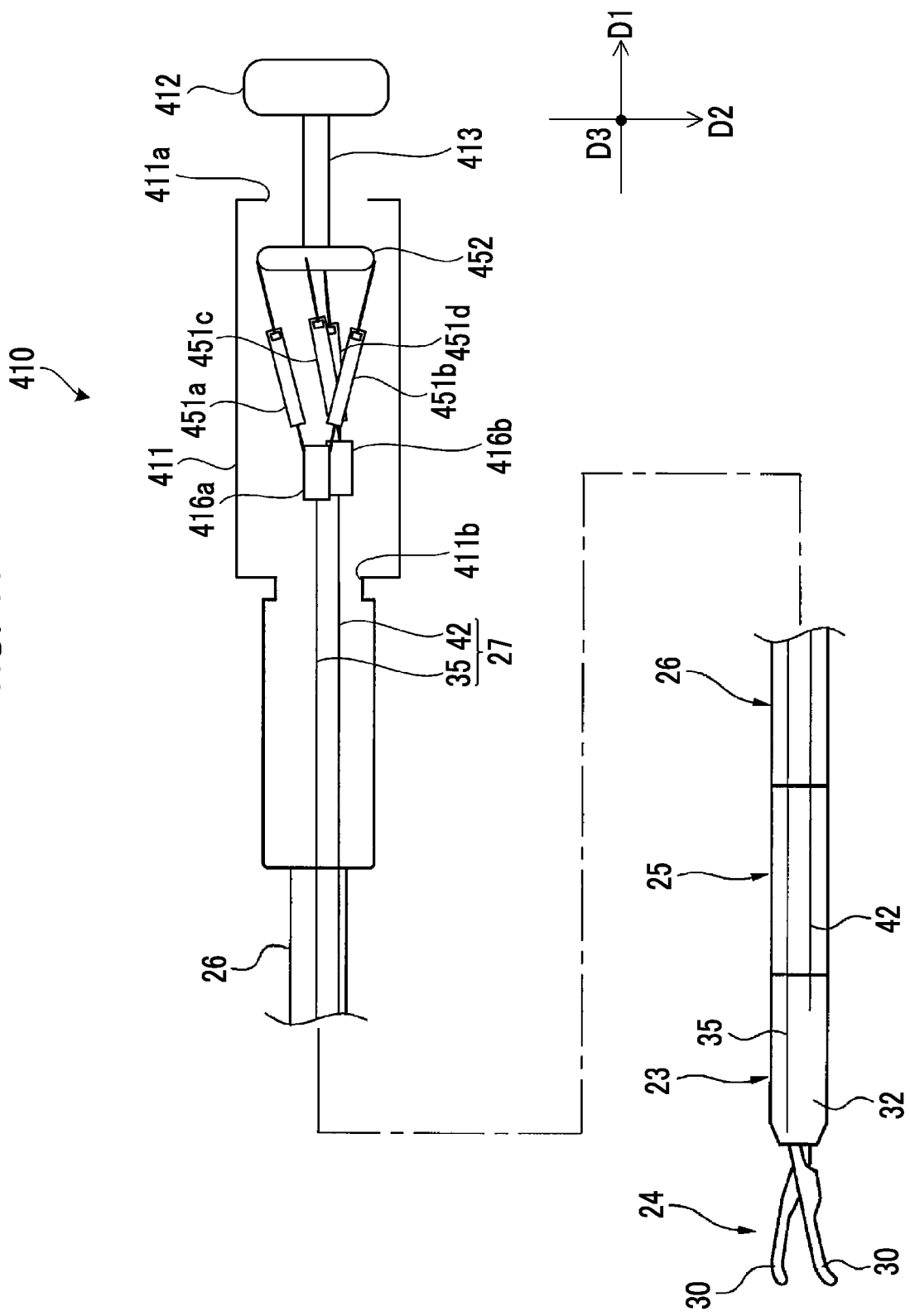
FIG. 44 is a view showing Modification Example 2 of the transmitting part and the operating part of the treatment tool for an endoscope, which is for describing Embodiment 2 of the present invention.

FIG. 44 is a view showing Modification Example 2 of the transmitting part and the operating part of the treatment tool for an endoscope, which is for describing Embodiment 2 of the present invention. For example, as shown in FIG. 44, a configuration where dampers 451*a* to 451*d* and a disk body 452 are provided in the configuration shown in FIGS. 41 to 43, instead of the wires 415*a* to 415*d* and the sphere 414, may be adopted. The dampers 451*a* to 451*d* are, for example, flexible stiff members using a piston. The disk body 452 is an example of a rotational movement body that is provided so as to be movable rotationally inside the gripped part 411 and is connected to the finger placing part 412 and the support column part 413.

The dampers 451*a* and 451*b* are examples of a first flexible member that is fixed to the disk body 452 (the rotational movement body) and is connected to the wire 35. The dampers 451*c* and 451*d* are examples of a second flexible member that is fixed to a portion of the disk body 452, which is different from the portions to which the dampers 451*a* and 451*b* are fixed and is connected to the wire 42.

Even though the dampers 451*a* to 451*d* are used instead of the wires 415*a* to 415*d*, in a case of performing an operation of tilting the finger placing part 412 and the support column part 413 with respect to the gripped part 411, the connecting portions 416*a* and 416*b* are pulled in the A-direction by pulling some of the dampers and other dampers shorten. Thus, the movements of the connecting portions 416*a* and 416*b* in the A-direction are not hindered.

Although a configuration where the disk body 452 is provided instead of the sphere 414 in order to make connecting the dampers 451*a* to 451*d*, which are stiff members, easier has been described, a configuration where the sphere 414 is provided instead of the disk body 452 may be adopted in the example of FIG. 44.

As described above, in the operating part 410 of Modification Example 2, by providing the dampers 451*a* to 451*d* (flexible members) instead of the wires 415*a* to 415*d*, the same effects as the operating part 410 of Modification Example 1 can be obtained. A configuration where any of the dampers 451*a* and 451*b* is omitted may be adopted. In addition, a configuration where any of the dampers 451*c* and 451*d* is omitted may be adopted.

The wires 415*a* and 415*b* are two wires fixed to the two portions of the surface of the sphere 414, which intersect the straight line passing through the rotational movement center of the sphere 414 in the D2-direction. By providing the wires 415*a* and 415*b*, the grip part 24 can be closed by pulling the wire 35 even though the finger placing part 412 and the support column part 413 are tilted to any side in the D2-direction. However, a configuration where one of the wires 415*a* and 415*b* is omitted may be adopted.

Each of the modification examples of the operating part described in Embodiment 2 is applicable to each configuration of Embodiment 1. For example, although a case where the grip part 24 is closed and the bendable part 25 is bent in response to an operation has been described in Embodiment 2, as in the example shown in Embodiment 1, a configuration where the grip part 24 is opened and the bendable part 25 is restored to a linear shape by performing a reverse operation may be adopted.

Although various types of embodiments have been described hereinbefore with reference to the drawings, it is evident that the present invention is not limited to such examples. It is clear that those skilled in the art can come up with various types of changed examples or modified examples within the scope of claims, and it is understood that those examples obviously belong to the technical scope of the present invention. In addition, without departing from the gist of the invention, each of components in the embodiments may be combined in any manner.

This application is based on the US provisional application filed on Sep. 6, 2019 (62/896,579) and the US provisional application filed on Aug. 12, 2020 (63/064,899), the content of which is incorporated herein by reference.

EXPLANATION OF REFERENCES

1: endoscope system
2: endoscope
3: light source device
4: processor
5: monitor
6: endoscope insertion part
7: endoscope operating part
8: universal cord
9: connector
10: endoscope distal end part
11: endoscope bendable part
12: endoscope soft portion
13: first treatment tool insertion opening
14: first treatment tool channel
15: second treatment tool insertion opening
16: second treatment tool channel
20: endoscope treatment tool
21: insertion part
22: operating part
23: distal end part
24: grip part
25: bendable part
26: soft portion
27: transmitting part
28: first transmitting member
29: second transmitting member
30: grip claw
31: link member
32: support
33: pin
34: pin
35: wire
40: cyclic member
40A: first portion
40B: second portion
41: pin
42: wire
43: first guide
44: second guide
45: elastic member
50: operating part body
51: operating member
52: plane portion
53: engaging part
54: side surface (engaging surface)
54: side surface
60: follower member
61: cam member
62: engaging part
63: side surface (engaging surface)
63: side surface
64: cam groove
64A: drive region
64B: holding region
64C: holding region
65: cam pin
66: locking part
70: operating part body 71: operating member
73: engaging part
74: side surface (engaging surface)
74: side surface
80: follower member
81: cam member
82: engaging part
83: side surface (engaging surface)
83: side surface
84: cam groove
84A: drive region
85: cam pin
90: high-frequency forcep
120: endoscope treatment tool
121: insertion part
125: bendable part
140: cyclic portion
140A: first portion
140B: second portion
141: connecting portion
320: endoscope treatment tool
321: insertion part
322: operating part
323: distal end part
324: grip part
325: bendable part
326: soft portion
327: transmitting part
328: first transmitting member
329: second transmitting member
330: grip claw
332: support
335: wire
340: cyclic member
340A: first portion
340B: second portion
341: pin
342: wire
343: first guide
344: second guide
350: operating part body
351: operating member
353: engaging part
360: follower member
361: cam member
362: engaging part
364: cam groove
364A: drive region
364B: holding region
364C: holding region
365: cam pin
366: locking part
410: operating part
411: gripped part
411$a$: opening portion
411$b$: opening portion
412: finger placing part
413: support column part
414: sphere
415$a$: wire
415$b$: wire
415$c$: wire
415$d$: wire
416$a$: connecting portion
416$b$: connecting portion
420: endoscope treatment tool
421: insertion part
425: bendable part
440: cyclic portion
440A: first portion
440B: second portion
441: connecting portion
451$a$: damper
451$b$: damper
451$c$: damper
451$d$: damper
452: disk body
GA: gap
GB: gap
LA: lesion part
S: bent neutral plane
x: rotational movement shaft
X: central axis

What is claimed is:

1. A treatment tool for an endoscope comprising:
an insertion part that has a distal end part, which is provided with an openable and closable grip part, and a bendable part, which is provided adjacent to the distal end part and is bendable, and that is insertable into a body;
an operating part into which an operation of closing the grip part and an operation of bending the bendable part are input; and
a transmitting part that transmits the operations of the operating part to the grip part and the bendable part,
wherein the operating part has an operating member that is movable in a first direction parallel to a longitudinal axis of the insertion part and a second direction orthogonal to the first direction,
the transmitting part has
a follower member that is movable only in the first direction among the first direction and the second direction,
a cam member that is movable only in the second direction among the first direction and the second direction and drives the follower member in the first direction in response to a movement of the cam member in the second direction,
a first transmitting member that extends from the operating member to the insertion part, and
a second transmitting member that extends from the follower member to the insertion part,
the operating member and the cam member have engaging parts respectively that allow a relative movement in the first direction and prevent a relative movement in the second direction by engaging with each other,
the grip part is closed as one of the first transmitting member or the second transmitting member is moved in the first direction, and
the bendable part is bent as other of the first transmitting member or the second transmitting member is moved in the first direction.

2. The treatment tool for an endoscope according to claim 1,
wherein each of the engaging part of the operating member and the engaging part of the follower member has an engaging surface that extends parallel to the first direction and intersects the second direction.

3. The treatment tool for an endoscope according to claim 1,
wherein the second direction is a linear direction in a plane including the first direction.

4. The treatment tool for an endoscope according to claim 3,
wherein the cam member has a cam groove,
the follower member has a cam pin that is engaged with the cam groove so as to be movable in an extending direction of the cam groove, and
the cam groove has a drive region that extends in a third direction intersecting the first direction and the second direction in the plane and a holding region that extends from at least one end of the drive region in the second direction.

5. The treatment tool for an endoscope according to claim 4,
wherein the cam groove has a locking part that locks the cam pin in the holding region.

6. The treatment tool for an endoscope according to claim 1,
wherein the second direction is a circumferential direction in a cylindrical plane about an axis which is same as or is parallel to the longitudinal axis, the cylindrical plane including the first direction.

7. The treatment tool for an endoscope according to claim 6,
wherein the cam member has a cam groove,
the follower member has a cam pin that is engaged with the cam groove so as to be movable in an extending direction of the cam groove, and
the cam groove has a drive region that extends in a third direction intersecting the first direction and the second direction in the cylindrical plane and a holding region that extends from at least one end of the drive region in the second direction.

8. The treatment tool for an endoscope according to claim 7,
wherein the cam groove has a locking part that locks the cam pin in the holding region.

* * * * *